United States Patent
Eby et al.

(10) Patent No.: US 11,541,243 B2
(45) Date of Patent: Jan. 3, 2023

(54) BIOSTIMULATOR HAVING COAXIAL FIXATION ELEMENTS

(71) Applicant: Pacesetter, Inc., Sylmar, CA (US)

(72) Inventors: Thomas B. Eby, Mountain View, CA (US); Tyler J. Strang, Valencia, CA (US); Keith Victorine, Valencia, CA (US); Wesley Alleman, Santa Clarita, CA (US)

(73) Assignee: PACESETTER, INC., Sylmar, CA (US)

(*) Notice: Subject to any disclaimer, the term of this patent is extended or adjusted under 35 U.S.C. 154(b) by 191 days.

(21) Appl. No.: 16/790,451

(22) Filed: Feb. 13, 2020

(65) Prior Publication Data

US 2020/0289835 A1    Sep. 17, 2020

Related U.S. Application Data

(60) Provisional application No. 62/903,482, filed on Sep. 20, 2019, provisional application No. 62/819,367, filed on Mar. 15, 2019.

(51) Int. Cl.
*A61N 1/37* (2006.01)
*A61N 1/375* (2006.01)

(52) U.S. Cl.
CPC ....... *A61N 1/37518* (2017.08); *A61N 1/3756* (2013.01); *A61N 1/37512* (2017.08)

(58) Field of Classification Search
CPC ............ A61N 1/37518; A61N 1/37512; A61N 1/3756; A61N 1/0573; A61N 2001/0578; A61N 1/3624
See application file for complete search history.

(56) References Cited

U.S. PATENT DOCUMENTS 3,943,936 A    3/1976    Rasor et al.
3,974,834 A    8/1976    Kane
(Continued)

FOREIGN PATENT DOCUMENTS

EP    1 835 962 B1    4/2015
EP    2 988 821 B1    8/2018
(Continued)

OTHER PUBLICATIONS

Extended European Search Report from related EP Application No. 20162284.2 dated Jul. 24, 2020 (5 pages).
(Continued)

*Primary Examiner* — Allen Porter
*Assistant Examiner* — Natasha Patel
(74) *Attorney, Agent, or Firm* — Womble Bond Dickinson (US) LLP

(57) ABSTRACT

A biostimulator, such as a leadless cardiac pacemaker, including coaxial fixation elements to engage or electrically stimulate tissue, is described. The coaxial fixation elements include an outer fixation element extending along a longitudinal axis and an inner fixation element radially inward from the outer fixation element. One or more of the fixation elements are helical fixation elements that can be screwed into tissue. The outer fixation element has a distal tip that is distal to a distal tip of the inner fixation element, and an axial stiffness of the outer fixation element is lower than an axial stiffness of the inner fixation element. The relative stiffnesses are based on one or more of material or geometric characteristics of the respective fixation elements. Other embodiments are also described and claimed.

21 Claims, 13 Drawing Sheets

(56) References Cited

U.S. PATENT DOCUMENTS

| | | |
|---|---|---|
| 4,106,512 A | 8/1978 | Bisping |
| 4,311,153 A | 1/1982 | Smits |
| 4,972,848 A | 11/1990 | Di Domenico et al. |
| 5,003,992 A | 4/1991 | Holleman et al. |
| 5,076,285 A | 12/1991 | Hess et al. |
| 5,575,814 A | 11/1996 | Giele et al. |
| 5,702,437 A | 12/1997 | Baudino |
| 5,716,391 A | 2/1998 | Grandjean |
| 5,741,321 A | 4/1998 | Brennen |
| 5,776,178 A | 7/1998 | Pohndorf et al. |
| 5,837,006 A | 11/1998 | Ocel et al. |
| 5,948,015 A | 9/1999 | Hess et al. |
| 6,489,562 B1 | 12/2002 | Hess et al. |
| 6,556,874 B2 | 4/2003 | Audoglio |
| 6,907,298 B2 | 6/2005 | Smits et al. |
| 6,909,920 B2 | 6/2005 | Lokhoff et al. |
| 6,931,285 B2 | 8/2005 | Bischoff |
| 6,931,286 B2 | 8/2005 | Sigg et al. |
| 7,027,876 B2 | 4/2006 | Casavant et al. |
| 7,082,335 B2 | 7/2006 | Klein et al. |
| 7,103,418 B2 | 9/2006 | Laske et al. |
| 7,127,302 B2 | 10/2006 | Palm |
| 7,158,838 B2 | 1/2007 | Seifert et al. |
| 7,187,971 B2 | 3/2007 | Sommer et al. |
| 7,274,966 B2 | 9/2007 | Sommer et al. |
| 7,313,445 B2 | 12/2007 | McVenes et al. |
| 7,363,091 B1 * | 4/2008 | Chen ............... A61N 1/0568 607/120 |
| 7,532,939 B2 | 5/2009 | Sommer et al. |
| 7,580,758 B2 | 8/2009 | Junge et al. |
| 7,599,747 B2 | 10/2009 | Feldmann et al. |
| 7,657,325 B2 | 2/2010 | Williams |
| 7,657,326 B2 | 2/2010 | Bodner et al. |
| 7,720,550 B2 | 5/2010 | Sommer et al. |
| 7,751,905 B2 | 7/2010 | Feldmann et al. |
| 7,844,348 B2 | 11/2010 | Swoyer et al. |
| 7,860,580 B2 | 12/2010 | Falk et al. |
| 7,937,161 B2 | 5/2011 | Hastings et al. |
| 7,942,917 B2 | 5/2011 | Nowak, Jr. |
| 7,967,857 B2 | 6/2011 | Lane |
| 3,057,459 A1 | 11/2011 | Rioux et al. |
| 8,135,467 B2 | 3/2012 | Markowitz et al. |
| 8,211,169 B2 | 7/2012 | Lane et al. |
| 8,219,209 B2 | 7/2012 | Arnholt et al. |
| 8,219,213 B2 | 7/2012 | Sommer et al. |
| 8,239,039 B2 | 8/2012 | Zarembo et al. |
| 8,313,621 B2 | 11/2012 | Goad et al. |
| 8,346,374 B2 | 1/2013 | Foster et al. |
| 8,412,351 B2 | 4/2013 | Zeijlemaker et al. |
| 8,457,742 B2 | 6/2013 | Jacobson |
| 8,478,429 B2 | 7/2013 | Walker et al. |
| 8,478,430 B2 | 7/2013 | Sommer et al. |
| 8,500,757 B2 | 8/2013 | Miraki et al. |
| 8,527,068 B2 | 9/2013 | Ostroff |
| 8,543,224 B2 | 9/2013 | Foster et al. |
| 8,560,087 B2 | 10/2013 | Foster |
| 8,634,912 B2 | 1/2014 | Bornzin et al. |
| 8,694,128 B2 | 4/2014 | Seifert et al. |
| 8,700,181 B2 | 4/2014 | Bornzin et al. |
| 8,755,909 B2 | 6/2014 | Sommer et al. |
| 8,812,134 B2 | 8/2014 | Foster et al. |
| 8,874,232 B2 | 10/2014 | Chen |
| 8,914,131 B2 | 12/2014 | Bornzin et al. |
| 8,923,985 B2 | 12/2014 | Clark et al. |
| 8,948,883 B2 | 2/2015 | Eggen et al. |
| 8,954,168 B2 | 2/2015 | Foster |
| 9,020,611 B2 | 4/2015 | Khairkhahan et al. |
| 9,056,180 B2 | 6/2015 | Powell et al. |
| 9,089,695 B2 | 7/2015 | Seifert et al. |
| 9,186,209 B2 | 11/2015 | Weber et al. |
| 9,216,285 B1 | 12/2015 | Boling et al. |
| 9,242,102 B2 | 1/2016 | Khairkhahan et al. |
| 9,265,436 B2 | 2/2016 | Min et al. |
| 9,272,155 B2 | 3/2016 | Ostroff |
| 9,333,342 B2 | 5/2016 | Haasl et al. |
| 9,333,344 B2 | 5/2016 | Foster |
| 9,358,387 B2 | 6/2016 | Suwito et al. |
| 9,421,384 B2 | 8/2016 | Taff et al. |
| 9,517,336 B2 | 12/2016 | Eggen et al. |
| 9,579,500 B2 | 2/2017 | Rys et al. |
| 9,682,230 B2 | 6/2017 | Zhang et al. |
| 9,694,172 B2 | 7/2017 | Foster et al. |
| 9,724,126 B2 | 8/2017 | Gerber et al. |
| 9,770,586 B2 | 9/2017 | Doerr et al. |
| 9,775,982 B2 | 10/2017 | Grubac et al. |
| 9,827,414 B2 | 11/2017 | Doerr et al. |
| 9,867,964 B2 | 1/2018 | Drake et al. |
| 9,899,778 B2 | 2/2018 | Hanson et al. |
| 9,907,952 B2 | 3/2018 | Sommer et al. |
| 9,907,953 B2 | 3/2018 | Orts et al. |
| 9,943,682 B2 | 4/2018 | Eggen et al. |
| 10,028,832 B2 | 7/2018 | Quill et al. |
| 10,046,167 B2 | 8/2018 | Schmidt et al. |
| 10,071,243 B2 | 9/2018 | Kuhn et al. |
| 10,080,887 B2 | 9/2018 | Schmidt et al. |
| 10,092,744 B2 | 10/2018 | Sommer et al. |
| 10,099,050 B2 | 10/2018 | Chen et al. |
| 10,449,354 B2 | 10/2019 | Demmer et al. |
| 2003/0065374 A1 | 4/2003 | Honeck |
| 2003/0114908 A1 | 6/2003 | Flach |
| 2004/0102830 A1 | 5/2004 | Williams |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0088418 A1 | 4/2007 | Jacobson |
| 2009/0005845 A1 * | 1/2009 | David ............... A61N 1/36114 607/122 |
| 2009/0082828 A1 | 3/2009 | Ostroff |
| 2009/0118776 A1 | 5/2009 | Kelsch et al. |
| 2009/0234368 A1 | 9/2009 | Gore |
| 2011/0071515 A1 * | 3/2011 | Faure ............... A61B 18/1492 606/33 |
| 2012/0116489 A1 | 5/2012 | Khairkhahan et al. |
| 2012/0185023 A1 * | 7/2012 | Clark ............... A61B 5/283 607/116 |
| 2013/0116738 A1 * | 5/2013 | Samade ............... A61N 1/3684 607/9 |
| 2013/0253532 A1 * | 9/2013 | Fueglister ............ A61B 17/3468 606/129 |
| 2014/0296955 A1 * | 10/2014 | Jang ............... A61N 1/056 607/127 |
| 2015/0025350 A1 | 1/2015 | Schnittker |
| 2015/0025612 A1 * | 1/2015 | Haasl ............... A61N 1/0573 607/127 |
| 2015/0051612 A1 | 2/2015 | Schmidt et al. |
| 2015/0051614 A1 | 2/2015 | Schmidt et al. |
| 2015/0374976 A1 * | 12/2015 | Regnier ............... A61N 1/3756 607/120 |
| 2016/0331325 A1 | 11/2016 | Munsinger et al. |
| 2016/0354600 A1 | 12/2016 | Kolberg et al. |
| 2017/0043155 A1 | 2/2017 | Marshall et al. |
| 2017/0072191 A1 * | 3/2017 | Ma ............... A61N 1/0573 |
| 2017/0106185 A1 | 4/2017 | Orts et al. |
| 2017/0119555 A1 | 5/2017 | Bayer |
| 2017/0120042 A1 | 5/2017 | Becker et al. |
| 2017/0165454 A1 | 6/2017 | Tuohy et al. |
| 2017/0189669 A1 | 7/2017 | Kamarajugadda et al. |
| 2017/0239464 A1 | 8/2017 | Taeubert et al. |
| 2017/0252035 A1 | 9/2017 | Miraki |
| 2018/0071543 A1 | 3/2018 | Taff et al. |
| 2018/0133464 A1 | 5/2018 | Taeubert et al. |
| 2018/0207434 A1 | 7/2018 | Webb et al. |
| 2018/0221014 A1 | 8/2018 | Darabian |
| 2018/0236244 A1 | 8/2018 | Stevenson et al. |
| 2018/0264262 A1 | 9/2018 | Haasl et al. |

(56) References Cited

U.S. PATENT DOCUMENTS

2019/0001119 A1* 1/2019 Schmidt .............. A61N 1/059
2019/0076664 A1 3/2019 Ollivier

FOREIGN PATENT DOCUMENTS

| EP | 3 106 201 B1 | 11/2018 |
| JP | 2013540022 A | 10/2013 |
| WO | 2007/047681 A2 | 4/2007 |
| WO | 2018204753 A1 | 11/2018 |

OTHER PUBLICATIONS

Japanese Office Action (with translation) from related JP Application No. 2020-042652 dated Feb. 2, 2021 (8 pages).
U.S. Appl. No. 62/582,125, filed Nov. 6, 2017, 54 pgs.
U.S. Appl. No. 62/637,257, filed Mar. 1, 2018, 69 pgs.
U.S. Appl. No. 62/646,247, filed Mar. 21, 2018, 71 pgs.
Extended European Search Report from related EP Application No. 21189258.3 dated Nov. 22, 2021 (5 pages).
Decision of Reusal from related JP Application No. 2020-042652 dated Jun. 8, 2021 (10 pages including translation).
Notice of Reasons for Refusal from related Japanese Application No. 2020-042652 dated Apr. 19, 2022 (4 pages including translation).
Communication under Rule 71(3) EPC (intention to grant) from related EP Application No. 21189258.3 dated Jul. 28, 2022 (5 pages).
Decision of Appeal from related JP Application No. 2020-042652 dated Sep. 20, 2022 (4 pages including translation).

* cited by examiner

BIOSTIMULATOR HAVING COAXIAL FIXATION ELEMENTS

This application claims the benefit of priority of U.S. Provisional Patent Application No. 62/819,367, filed on Mar. 15, 2019, and US. Provisional Patent Application No. 62/903,482, filed on Sep. 20, 2019, both titled "Biostimulator Having Coaxial Fixation Elements," which are incorporated herein by reference in their entirety to provide continuity of disclosure.

BACKGROUND

Field

The present disclosure relates to biostimulators. More specifically, the present disclosure relates to leadless biostimulators having tissue anchors.

BACKGROUND INFORMATION

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The pulse generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Pacemaker electrode leads can be fixed to an intracardial implant site by an engaging mechanism such as an anchor. For example, the anchor can screw into the myocardium.

SUMMARY

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

Leadless cardiac pacemakers incorporate electronic circuitry at the pacing site and eliminate leads, and thus, avoid the above-mentioned shortcomings of conventional cardiac pacing systems. Leadless cardiac pacemakers can be anchored at the pacing site by an anchor that can screw into the target tissue. Existing anchors for leadless cardiac pacemakers, however, may damage the target tissue over time or may ineffectively secure the leadless cardiac pacemaker to the target tissue, which can lead to long-term reliability issues.

A biostimulator, such as a leadless cardiac pacemaker, having coaxial fixation elements to engage a target tissue, is provided. The coaxial fixation elements can secure the biostimulator to the target tissue and can retain the tissue against an electrode of the biostimulator (which may be one of the fixation elements) for reliable long-term pacing. In an embodiment, a biostimulator includes an outer fixation element and an inner fixation element coupled to a housing. The housing can having a longitudinal axis that both the inner fixation element and the outer fixation element extend about. More particularly, the fixation elements can include respective helices that extend about the longitudinal axis to respective distal tips. The fixation elements can be coaxial. For example, an inner helix of the inner fixation element can be radially inward of an outer helix of the outer fixation element. The outer fixation element can have a first distal tip axially offset from a second distal tip of the inner fixation element. For example, the first distal tip can be distal to the second distal tip.

The fixation elements can have respective mechanical characteristics. For example, the outer fixation element may be less stiff than the inner fixation element, e.g., along the longitudinal axis. In an embodiment, the outer fixation element has a lower spring constant than the inner fixation element. Accordingly, when the outer fixation element engages tissue, it can compress axially to bring the inner fixation element into tissue contact.

The pitches of the fixation element helices may be the same or different. For example, a first pitch of the outer helix can be equal to the second pitch of the inner helix. Accordingly, the fixation elements can advance into tissue at a same screw rate during implantation.

In an embodiment, the biostimulator includes a helix mount and a cup. The outer fixation element can be mounted on the helix mount, and the inner fixation element can be mounted on the cup. The helix mount can connect the outer fixation element to the housing of the biostimulator, and the cup can connect the inner fixation element to the housing. In an embodiment, the cup contains a filler, e.g., a therapeutic agent in a silicone matrix. The filler can be retained in the cup by the inner fixation element. For example, the inner fixation element can have an inner dimension that is less than an outer dimension of the filler. Accordingly, when the filler is loaded into the cup, and the inner fixation element is mounted on the cup over the filler, the filler can elute therapeutic agent through the inner fixation element, however, the fixation element constrain the filler within the cup.

The helix mount can be mounted on a flange of the housing. In an embodiment, the flange has interrupted external threads that mate to the helix mount. For example, the helix mount can have slotted keyways that receive the interrupted external threads to allow the helix mount to be dropped onto the flange. When the helix mount is placed over the flange, the flange can be rotated relative to the helix mount to cause the interrupted external threads to tap into an inner surface of the helix mount. The helix mount can therefore secure to the flange to secure a header assembly having the fixation elements to the housing of the biostimulator.

The fixation elements can have characteristics to improve device robustness. For example, the inner fixation element can have a flat coil section to provide a weld interface with the cup. The flat coil section can extend about the longitudinal axis, e.g., circumferentially, from a helical coil section of the fixation element. The flat coil section can extend circumferentially around an inner rim of the cup, and thus, a robust weld can be formed along the circumferential interface between the cup and the flat coil section.

In an embodiment, the distal tips of the coaxial fixation elements have a predetermined relative orientation. For example, the first distal tip can be on a first side of a first plane containing the longitudinal axis, and the second distal tip can be on a second side of the first plane. The distal tips can be diametrically opposed to each other. For example, a second plane containing the longitudinal axis and orthogonal to the first plane may also contain the first distal tip of the outer fixation element and the second distal tip of the inner fixation element.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
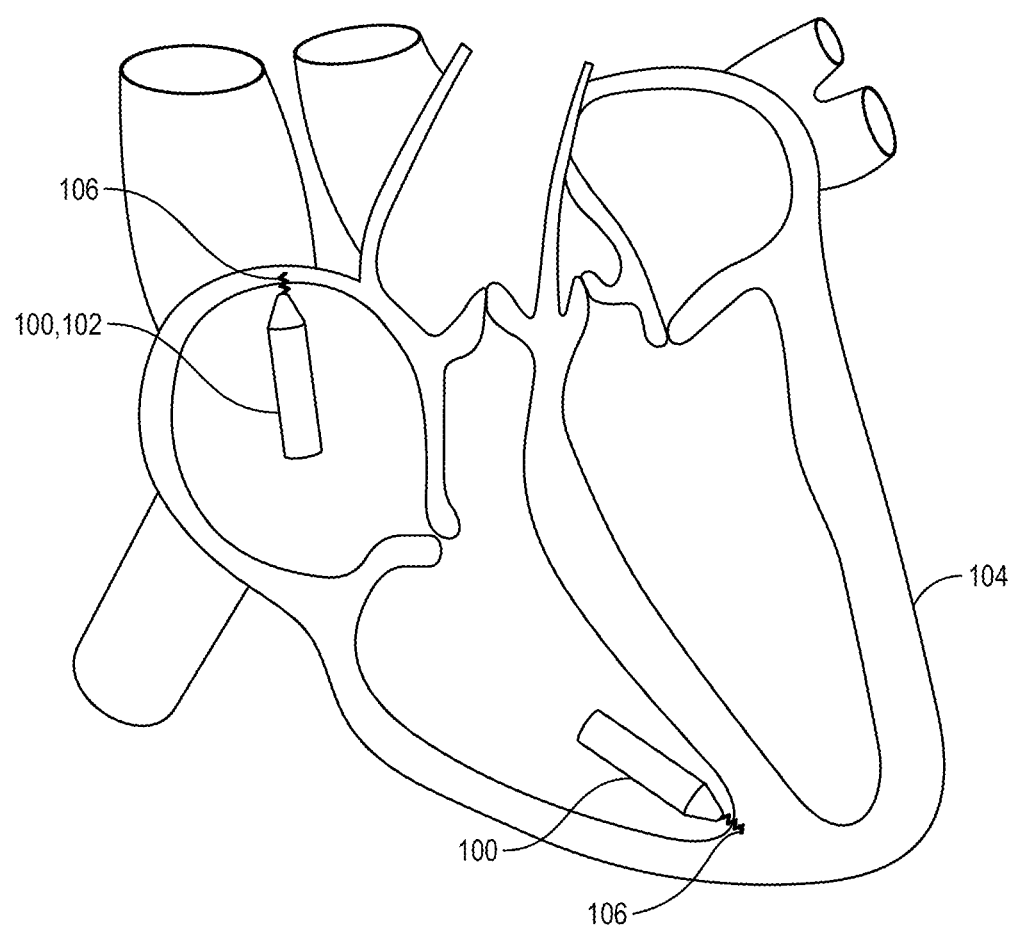
FIG. 1 is a diagrammatic medial-lateral cross section of a patient heart illustrating an example implantation of biostimulators in the patient heart, in accordance with an embodiment.

Embodiments describe a biostimulator, e.g., a leadless cardiac pacemaker, having coaxial fixation elements. The fixation elements include an inner fixation element radially inward from an outer fixation element, and the fixation elements can extend helically about a same longitudinal axis to respective distal tips. More particularly, the outer fixation element can extend to a first distal tip that is distal to a second distal tip of the inner fixation element. The fixation elements have respective axial stiffnesses based on respective characteristics, e.g., material or geometric characteristics, and a stiffness of the outer fixation element can be less than a stiffness of the inner fixation element. The biostimulator may be used to pace cardiac tissue as described below. The biostimulator may be used in other applications, such as deep brain stimulation, and thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal"

may indicate a first direction along a longitudinal axis of a biostimulator housing. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator is provided. The biostimulator includes coaxial fixation elements to engage tissue for anchoring the biostimulator within a patient anatomy. The fixation elements can have distal tip locations and axial stiffnesses that differ. For example, an outer fixation element can have a first distal tip that is distal to a second distal tip of an inner fixation element, and the outer fixation element can be less stiff in an axial direction than the inner fixation element. The differences in the fixation elements can allow the outer fixation element to engage and anchor within a target tissue prior to engaging and anchoring the inner fixation element within the target tissue. Furthermore, the fixation elements can engage the target tissue in a complementary manner that reduces a likelihood of disengagement between the tissue and an electrode of the biostimulator. In some embodiments, the inner fixation element is a portion of the electrode.

Referring to FIG. 1, is a diagrammatic medial-lateral cross section of a patient heart illustrating an example implantation of biostimulators in the patient heart is shown in accordance with an embodiment. A leadless biostimulator system, e.g., a cardiac pacing system, includes one or more biostimulators 100. The biostimulators 100 can be implanted in the patient heart 104, and can be leadless, and thus may be leadless cardiac pacemakers 102. Each biostimulator 100 can be placed in a cardiac chamber, such as a right atrium and/or right ventricle of the patient heart 104, or attached to an inside or outside of the cardiac chamber. Attachment of the biostimulator 100 to the cardiac tissue can be accomplished via one or more fixation elements 106, such as the coaxial fixation elements described below. In a particular embodiment, the leadless cardiac pacemaker 102 can use two or more electrodes located on or within a housing of the leadless cardiac pacemaker 102 for pacing the cardiac chamber upon receiving a triggering signal from at least one other device within the body. In an embodiment, one or more of the fixation elements 106 is an active electrode.

Leadless pacemakers or other leadless biostimulators can be delivered to or retrieved from a patient using delivery or retrieval systems. The leadless biostimulator system can include delivery or retrieval systems, which may be catheter-based systems used to carry a leadless biostimulator intravenously to or from a patient anatomy. The delivery or retrieval systems may be referred to collectively as transport systems. In some implementations of transport systems, a leadless pacemaker is attached or connected to a distal end of a catheter and advanced intravenously into or out of the heart 104. The transport system can include features to engage the leadless pacemaker to allow fixation of the leadless pacemaker to tissue. For example, in implementations where the leadless pacemaker includes an active engaging mechanism, such as the coaxial fixation elements described below, the transport system can include a docking cap or key at a distal end of the catheter, and the docking cap or key may be configured to engage the leadless pacemaker and apply torque to screw the active engaging mechanism into or out of the tissue. In other implementations, the transport system includes clips designed to match the shape of a feature on the leadless pacemaker and apply torque to screw the active engaging mechanism into or out of the tissue.

Figure 2:
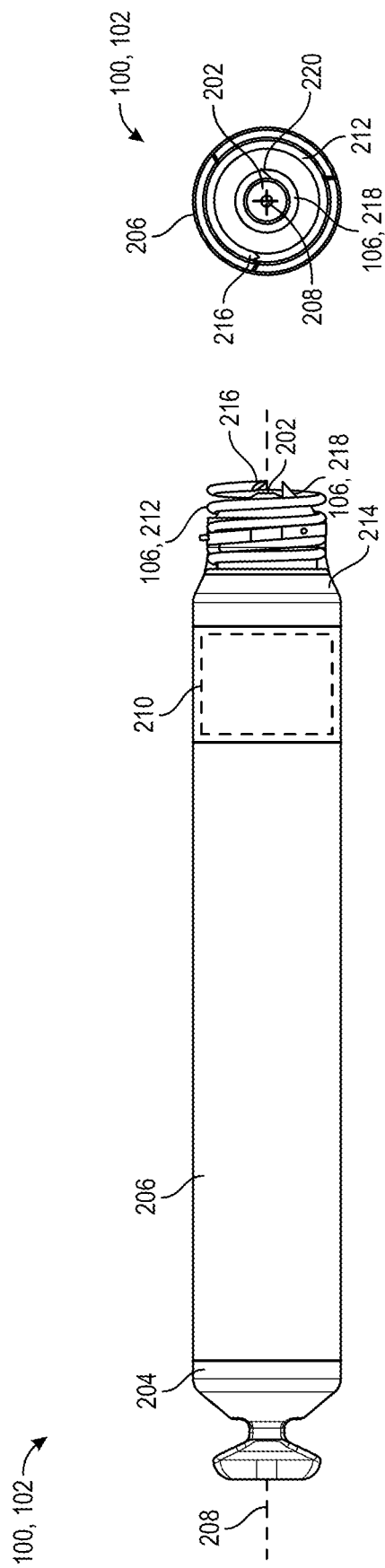
FIGS. 2A-2B are, respectively, side and end views of a biostimulator having coaxial fixation elements, in accordance with an embodiment.

Referring to FIG. 2A, a side view of a biostimulator having coaxial fixation elements is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes. e.g., a distal electrode 202 and a proximal electrode 204, located within, on, or near a housing 206 of the biostimulator 100. The distal electrode 202 can be a dome-shaped electrode that is centrally located along the central axis 208. In an embodiment, one or more of the fixation elements 106 (212 and/or 218) forms at least a portion of the distal electrode 202. For example, an inner fixation element 218 can act as an electrode. In certain embodiments, inner fixation element 218 is the only distal electrode. For example, the dome-shaped electrode 202 may be omitted and/or may be a smooth distal surface of the biostimulator 100 that does not serve an electrical function. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example, bidirectional communication. The housing 206 can optionally contain an electronics compartment 210 (shown by hidden lines) to hold circuitry adapted for different functionality. For example, the electronics compartment 210 can contain circuits for sensing cardiac activity from the electrodes, circuits for receiving information from at least one other device via the electrodes, circuits for generating pacing pulses for delivery to tissue via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers 102 or other leadless biostimulators 100 can be fixed to an intracardial implant site by one or more actively engaging mechanism or fixation mechanism, such as a screw or helical member that screws into the myocardium. In an embodiment, the biostimulator 100 includes the outer fixation element 212 coupled to the housing 206. The outer fixation element 212 can be a helical element to screw into target tissue. More particularly, the outer fixation element 212 can extend helically from a flange 214 of the biostimulator 100, which is mounted on the housing 206, to a distal end at a first distal tip 216 of the helix. The first distal tip 216 can be located distal to the distal electrode 202 (an inner fixation element 218 and/or another centrally located electrode). Accordingly, when the biostimulator 100 contacts the target tissue, the first distal tip 216 can pierce the tissue and the housing 206 can be rotated to screw the outer fixation element 212 into the target tissue to pull the distal electrode 202 into contact with the tissue.

Figure 5:
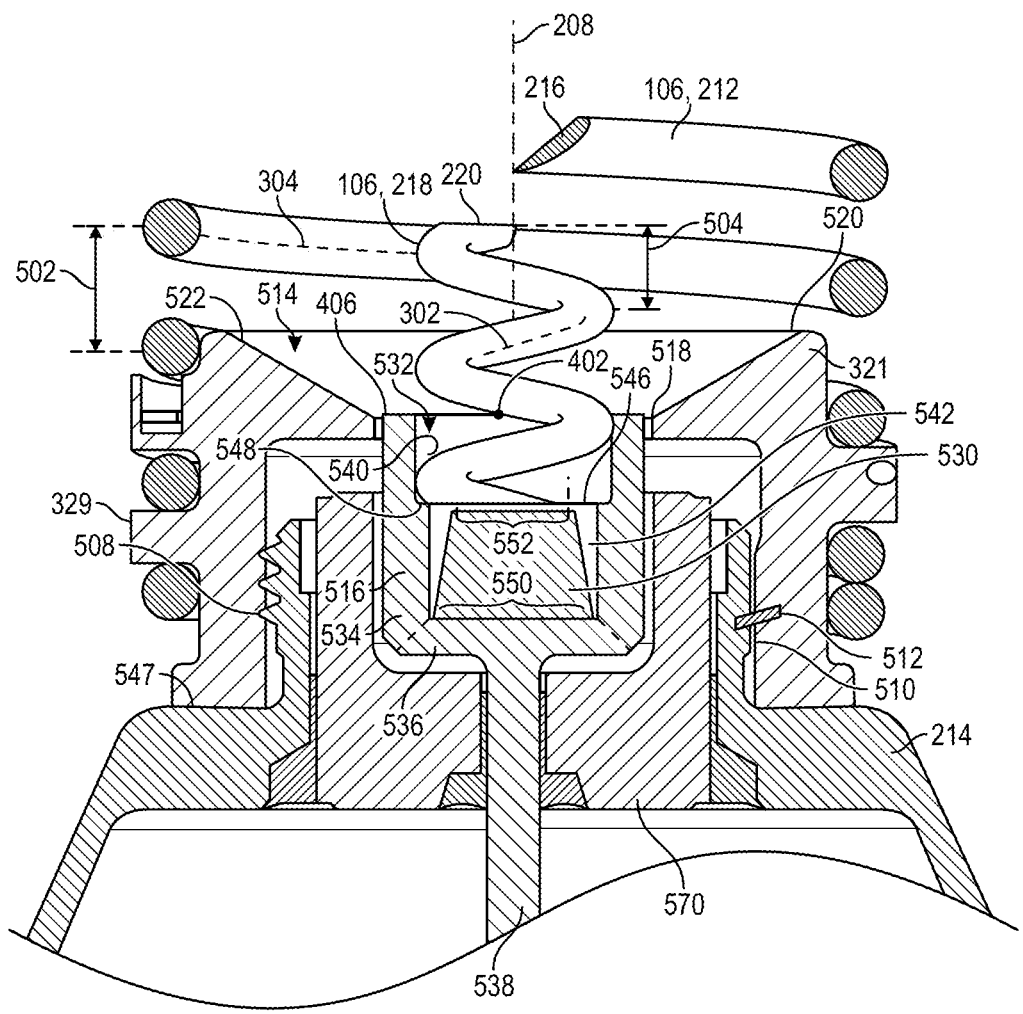
FIG. 5 is a cross-sectional view of a distal portion of a biostimulator having coaxial fixation elements, in accordance with an embodiment.

Referring to FIG. 2B, an end view of a biostimulator having coaxial fixation elements is shown in accordance with an embodiment. The biostimulator 100 can include the inner fixation element 218 coupled to the housing 206. The inner fixation element 218 can be coaxially arranged with the outer fixation element 212 about the longitudinal axis 208. More particularly, the inner fixation element 218 can extend helically about the longitudinal axis 208 at a location that is radially inward from the outer fixation element 212. The inner fixation element 218 can extend distally to a second distal tip 220. The second distal tip 220 may be proximal to the first distal tip 216, and thus, the first distal tip 216 can be distal to the second distal tip 220 (FIG. 5). The inner fixation element 218 can be a helical element to screw into target tissue. Accordingly, when the outer fixation element 212 screws into the tissue, the inner fixation element 218 can also engage the target tissue, and the housing 206 can be rotated to cause the second distal tip 220 of the inner fixation element 218 to pierce the tissue and anchor the biostimulator 100.

The inner fixation element 218 can be an active electrode, and can electrically communicate with the circuitry contained in the electronics compartment 210. Accordingly, the anchored inner fixation element 218 can electrically communicate with the tissue, and can transmit electrical pulses between the tissue and the circuitry of the biostimulator 100. To facilitate electrical function of the inner fixation element 218, the element may be coated in titanium nitride to reduce a polarization value of the electrode. By way of example, the titanium nitride coating may be in a range of 5 to 50 microns, e.g., 13 microns.

Figure 3:
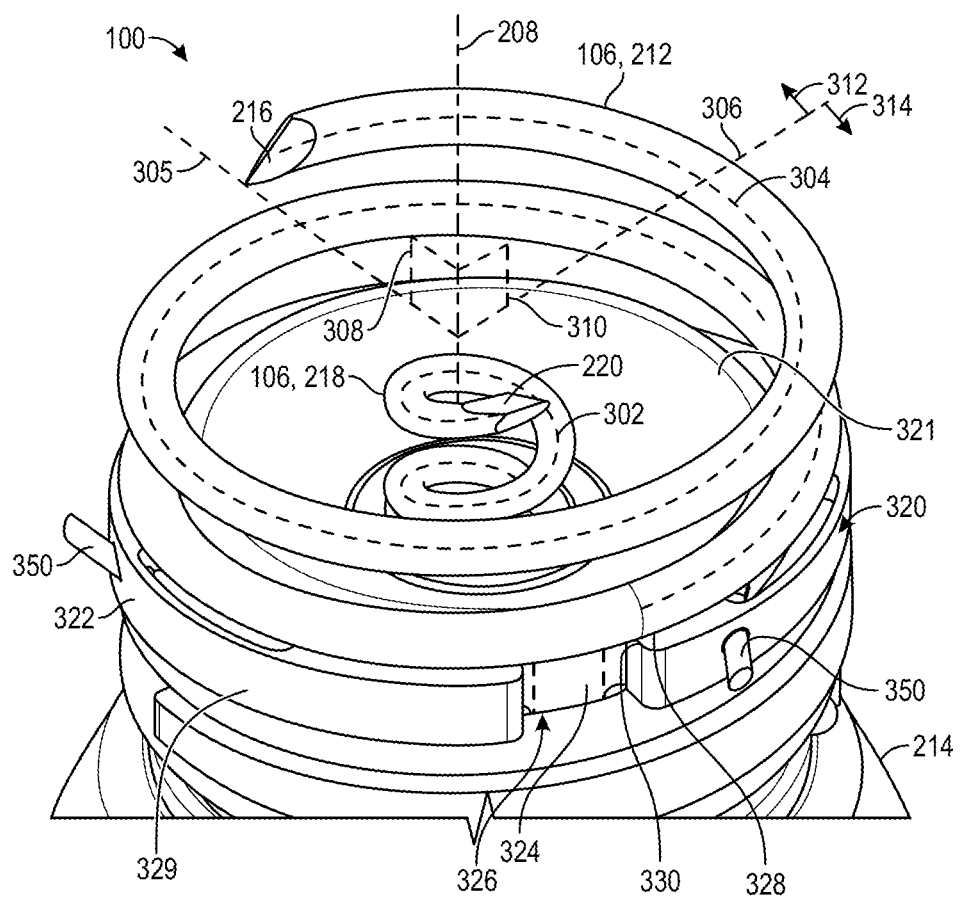
FIG. 3 is a perspective view of a distal portion of a biostimulator having coaxial fixation elements, in accordance with an embodiment.

Referring to FIG. 3, a perspective view of a distal portion of a biostimulator having coaxial fixation elements is shown in accordance with an embodiment. The biostimulator 100 can include the inner fixation element 218 nestled within the outer fixation element 212. More particularly, the inner fixation element 218 can include an inner helix 302 that is radially inward from an outer helix 304 of the outer fixation element 212. The helices can both extend or revolve about the longitudinal axis 208, and the fixation elements 106 can extend along the respective helices. A helix radius of the outer fixation element 212 may be greater than the helix radius of inner fixation element 218. As described below, the helices can have relative configurations that contribute to tissue piercing.

In an embodiment, the helices have a same clocking relative to the longitudinal axis 208. More particularly, the inner helix 302 and the outer helix 304 can revolve about the longitudinal axis 208 in a same direction. For example, both helices of the fixation elements 212, 218 may extend about the longitudinal axis 208 in a counterclockwise, e.g., a right-handed, direction to the respective distal tips 216, 220. Similar clocking of the helices can cause the fixation elements 212, 218 to simultaneously advance or retract from the target tissue when the biostimulator 100 is rotated. Alternatively, the helices may revolve about the longitudinal axis 208 in different directions.

The relative orientation characteristics of the fixation elements 106 can be predetermined. For example, the distal tips of the fixation elements 106 may terminate at different radial directions from the longitudinal axis 208, and an angular separation between the termination points can be controlled. It is contemplated that a greater angular distance between the distal tips of the fixation elements 106 can contribute to the fixation elements 106 gaining greater purchase in the target tissue. The maximized separation can make it easier to torque the fixation elements 106 into the tissue, and as the fixation elements 106 screw into the tissue there is less chance that tunnels formed by the advancing fixation elements 106 will intersect within the tissue. Accordingly, a distance and an angular separation between the distal tips 216, 220 can be maximized to enhance tissue engagement.

A geometric reference system can be established according to relative positions of the distal tips 216, 220 to the longitudinal axis 208. The reference system can include a first transverse axis 305 extending through the first distal tip 216 and orthogonal to the longitudinal axis 208. The reference system can also include a second transverse axis 306 extending orthogonal to both the longitudinal axis 208 and the first transverse axis 305. The reference system can include several planes defined by convention relative to the axes. For example, a first plane 308 (a portion of which is shown) can contain the longitudinal axis 208 and the first transverse axis 305. Similarly, a second plane 310 (a portion of which is shown) can contain the longitudinal axis 208 and the second transverse axis 306. Thus, the first plane 308 and the second plane 310 can be orthogonal planes that intersect along the longitudinal axis 208.

In an embodiment, the first distal tip 216 of the outer fixation element 212 is on a first side 312 of the second plane 310. It can be understood with reference to FIG. 3 that the first side 312 contains a distal segment of the outer fixation element 212 leading up to the first distal tip 216. By contrast, the second distal tip 220 is on a second side 314 of the second plane 310. The second side is opposite of the first distal tip 216, and thus, the second plane 310 separates the first distal tip 216 from the second distal tip 220.

An angle between the termination points of the distal tips can be a predetermined angle. In an embodiment, the first distal tip 216 can be located at a zero-degree position relative to the longitudinal axis 208 when viewed from above. More particularly, when viewed from above, the first axis can define a zero-degree position with respect to the longitudinal axis 208. When the second distal tip 220 is located on an opposite side of the second plane 310 from the first distal tip 216, the second distal tip 220 may therefore be between a 90-degree position and a 270-degree position (measured counterclockwise from the zero-degree position). In an embodiment, the first plane 308 contains the longitudinal axis 208, the first distal tip 216, and the second distal tip 220. Accordingly, the second distal tip 220 can be located at a 180-degree position 216, 220. The distal tips 216, 220 can be diametrically offset. Placement at the 180-degree position can maximize an angular separation between the distal tips. Other orientations are possible, however. For example, both distal tips can be located along a same radial line extending radially outward from the longitudinal axis 208 (the distal tips can be at a same angular position).

The distal tips of the coaxial fixation elements 106 can have relative height characteristics. For example, the first distal tip 216 of the outer fixation element 212 may be distal to the second distal tip 220 of the inner fixation element 218. More particularly, a piercing tip 216 of the outer fixation element 212 can be offset from a piercing tip 220 of the inner fixation element 218 in a direction of the longitudinal axis 208. It is contemplated that the projection of the outer fixation element 212 beyond the inner fixation element 218 can be varied based on a tissue type that is targeted and/or a target anatomy. For example, the offset height between the first distal tip 216 and the second distal tip 220 may be more or less depending on whether pectinated or non-pectinated tissue is targeted and/or whether the biostimulator 100 is configured for delivery to the sinus node, or right atrium, or right ventricle locations. Specific embodiments of offset height dependencies are provided below by way of example.

In an embodiment, ventricular locations can be targeted. For example, the atrioventricular node or the his-bundle may be targeted for pacing. The his-bundle is typically buried 1-5 cm deep into the heart tissue within a collagen canal. The clinical intravascular approach to this target site may be from the inferior vena cava and into the right atrium, however, right ventricular approaches and implantations may be possible with sufficiently designed delivery tools coupled to appropriately formed leadless pacemakers. The mitral valve annulus is close (<10 mm) to the ideal penetration location, and may be considered for long term device stabilization or negative hemodynamic effects due to implantation. Due to the depth and topographical form of the right atrium and right ventricle in these access locations, a large offset between the stimulation electrode and the stabilization anchor (inner fixation element 218 and outer fixation element 212 respectively) may be used to both penetrate deep enough into the nerve bundle and to stabilize the device. The offset may need to be of sufficient height to reduce a likelihood or minimize the piercing, rubbing, or other contact between adjacent tissue structures, e.g., the aorta, outside of the target location(s).

With the above background, it will be appreciated that the inner fixation element 218 may need to penetrate to a depth of 3-5 cm to pace the his-bundle. By contrast, the outer fixation element 212 may only be needed for fixation, e.g., to grip the tissue, and may not have to penetrate the target tissue to the same depth as the inner fixation element 218. Accordingly, the distal tip 220 of the inner fixation element 218 may extend beyond the distal tip 216 of the outer fixation element 212. It is noteworthy that, in such case, impedance may be increased due to the lengthened inner fixation element 218. To reduce a likelihood that impedance is increased by the longer fixation element 106, a proximal end of the inner fixation element 218 may be masked. For example, a portion of the inner fixation element 218 that is within an envelope of the outer fixation element 212 may be masked to avoid an increase in impedance. Masking a portion of the inner fixation element 218 can reduce the surface area exposed to the surrounding environment and tissue, and thus, the impedance can be correspondingly increased to compensate for the lengthened fixation element 218.

An increased offset between the inner and outer fixation element tips may also be used in other use cases. For example, a positive offset between the tips, e.g., the distal tip 220 of the inner fixation element 218 extending beyond the distal tip 216 of the outer fixation element 212, may be used in sinoatrial node pacing, or in septal wall pacing to overcome left bundle branch block.

A negative offset between the distal tips of the fixation elements, e.g., in which the distal tip 216 of the outer fixation element 212 extends beyond the distal tip 220 of the inner fixation element 218, may be beneficial in certain use cases. For example, in thin tissue such as the tissue of an atrium, care should be taken to not pierce through the atrial wall into the pericardial space. If the inner fixation element 218 extends into the pericardial space, the pericardial fluid could cause a drop in impedance, which may have a negative impact on device functionality, e.g., longevity. Accordingly, the inner fixation element 218 can have a distal tip 220 that is proximally offset from the distal tip 216 of the outer fixation element 212.

During use, e.g., when the biostimulator 100 is pressed against the target tissue, the axial offset between the piercing tips can reduce. For example, when the first distal tip 216 contacts the target tissue, advancement of the housing 206 can compress the outer fixation element 212 until the piercing tip 220 of the inner fixation element 218 also contacts the target tissue (or vice versa when tip 220 is initially distal to tip 216). Axial compression of the fixation elements 106 can depend on respective stiffnesses of the elements.

In an embodiment, a first stiffness of the outer fixation element 212 in the direction of the longitudinal axis 208 is less than a second stiffness of the inner fixation element 218 in the direction of the longitudinal axis 208. Accordingly, a spring rate of the outer fixation element 212 can be less than a spring rate of the inner fixation element 218 such that a same axial load produces more axial deformation of the outer fixation element 212 than the inner fixation element 218. More particularly, the outer fixation element 212 can have a lower spring constant than the inner fixation element 218.

The relative stiffnesses of the coaxial fixation elements 106 can be based on one or more of several factors. For example, the stiffness of each fixation element 106 can be based on a combination of material characteristics, overall geometry of the fixation elements 106 (helix pitch, wire diameter, major diameter, etc.), or any other bulk characteristic of the fixation elements 106.

The outer fixation element 212 can be less axially stiff than the inner fixation element 218 in part due to material characteristics of the helical elements. In an embodiment, the difference in spring constants can, but does not necessarily, correlate to a difference in elastic moduli of the fixation elements 106. For example, a material of the outer fixation element 212 may have a higher or lower elastic modulus than a material of the inner fixation element 218. Both of the fixation elements 106 can be formed of metallic biocompatible materials including, without limitation, stainless steel, nickel titanium alloys, nickel cobalt alloys, or platinum iridium. For example, the outer fixation element 212 may include a wire coil formed from MP35N nickel cobalt alloy, and the inner fixation element 218 may include a wire coil formed from an 80/20 platinum iridium alloy. The MP35N alloy may have a higher elastic modulus, e.g., 28,500 ksi, as compared to the elastic modulus of the platinum iridium alloy, e.g., 26,800 ksi.

The outer fixation element 212 can be less axially stiff than the inner fixation element 218 in part due to geometry of the fixation elements 106. In an embodiment, the inner fixation element 218 has a larger cross-sectional area, e.g., transverse to the helical axis of the coiled wire forming the fixation element, than a counterpart cross-sectional area of the outer fixation element 212. Accordingly, even when the fixation elements are formed from materials having similar elastic moduli, the larger section modulus of the inner fixation element 218 can result in a stiffer structure than the outer fixation element 212.

FIG. 3 has primarily been referred to for the above discussion of relative orientations between fixation elements 106, however, the illustration more broadly shows various features of a header assembly 320 mounted on the flange 214 of the housing 206.

The header assembly 320 includes the outer fixation element 212 mounted on a helix mount 321. The helix mount 321 includes features that interact with the housing 206, the outer fixation element 212, and the target tissue. In an embodiment, the helix mount 321 includes a helix mount flange 322. The helix mount flange 322 can extend radially outward from the helix mount body 324. The helix mount flange 322 can act as a mounting thread that extends around the longitudinal axis 208 and the helix mount body 324. A mounting thread structure of the helix mount flange 322 can be helical such that spiraling turns of the helix mount flange 322 are separated by helix mount gaps that also spiral about the longitudinal axis 208. The outer fixation element 212 can be received within the threaded groove (the helix mount gaps) of helix mount 321 as shown. For example, an assembler can insert a proximal end of the outer fixation element 212 into a distal end of the helical gap and rotate the outer fixation element 212 relative to the helix mount 321 to cause the helical fixation element to advance along and thread onto the helix mount 321.

In addition to having turns that are separated from each other by the helix mount gaps in the longitudinal direction, the helix mount flange 322 can have one or more interruptions in the helical direction. For example, the helix mount flange 322 can extend around the longitudinal axis 208 to a flange notch 326. The flange notch 326 can be an indentation or recess in a radially outward surface 329 of the helix mount flange 322. In an embodiment, the flange notch 326 is a datum feature used to inspect for a location of an outer pinch point 328. More particularly, when the outer fixation element 212 is mounted on the helix mount flange 322, the outer pinch point 328 is the location at which first contact is made between the outer fixation element 212 and the helix mount flange 322.

The outer pinch point 328 can be a predetermined angular distance from the first distal tip 216. For example, the biostimulator 100 may be designed such that the first distal tip 216 is 1.5 turns from the outer pinch point 328. Given that the pitch of the outer fixation element 212 can be gradual, it may be difficult to identify the exact location of the pinch point 328 during manufacture. That is, the contact point between the outer fixation element 212 and an upper surface of the helix mount flange 322 may not be readily discernible. The flange notch 326, however, creates a proximal edge 330 on the helix mount flange 322 that can be visually identified. Accordingly, an assembler can determine that the outer fixation element 212 first contacts the helix mount flange 322 at or near the proximal edge 330 of the flange notch 326. By determining that the outer pinch point 328 is at the flange notch 326, the angular separation between the outer pinch point 328 and the first distal tip 216 can be verified. More particularly, the number of turns between the pinch point 328 and the first distal tip 216 can be seen (and is 1.5 turns in FIG. 3).

The header assembly 320 can include one or more secondary fixation elements 350. The second fixation elements 350 can be one or more of a thread, filament, suture, or other elongated structure that extends radially outward from the radially outward surface 329 of the helix mount flange 322. Secondary fixation elements 350 can have radial and tangential components relative to the radially outward surface 329. For example, secondary fixation elements 350 can extend at an angle from the radially outward surface 329 with a particular clocking, e.g., opposite to the clocking of the outer fixation element 212. When the second fixation element 350 extends opposite to the fixation elements 106, the secondary fixation elements 350 can resist back out by engaging tissue around the biostimulator 100 when the coaxial fixation elements 106 are engaged with the target tissue.

Figure 4:
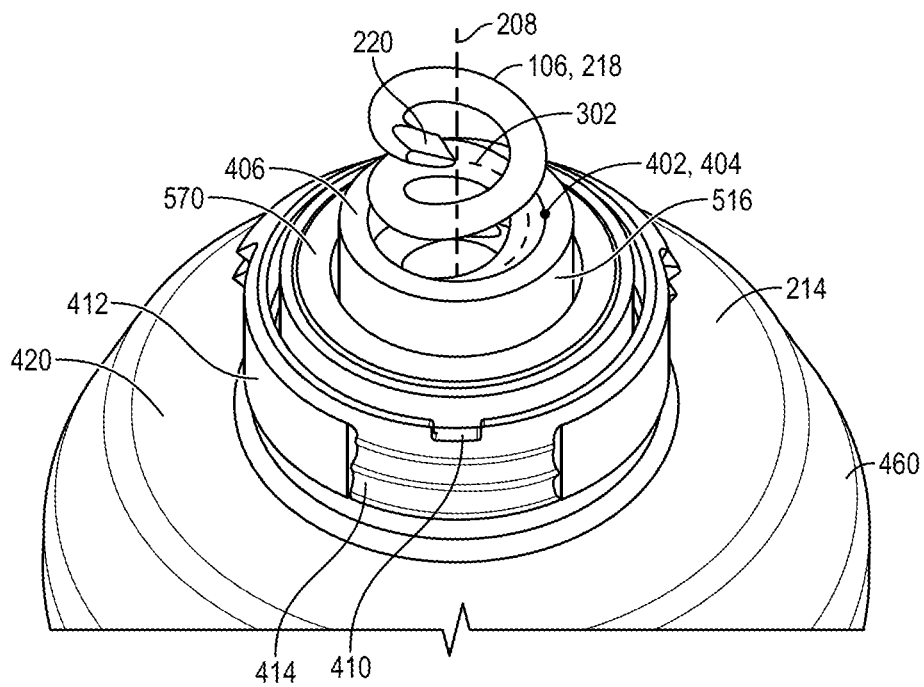
FIG. 4 is a perspective view of a distal portion of a biostimulator having a removed header assembly, in accordance with an embodiment.

Referring to FIG. 4, a perspective view of a distal portion of a biostimulator having a removed header assembly is shown in accordance with an embodiment. In addition to the helix mount 321 and the outer fixation element 212, the header assembly 320 can include the flange 214, an electrode having a cup 516, and the inner fixation element 218 mounted on and electrically coupled to the cup 516. The header assembly 320 can also include an insulator (FIG. 5) physically separating and electrically isolating the flange 214 from the cup 516.

The inner fixation element 218 can be connected to the cup 516 in any of various manners, such as by thermally or adhesively welding the fixation element to the cup 516. In an embodiment, the inner fixation element 218 is attached to the cup 516 by a weld 402, e.g., a spot weld. The weld 402 can join the cup 516 to the inner fixation element 218 to cause the components to act as a unitary body under mechanical fatigue, e.g., when the inner fixation element 218 is engaged in pulsating tissue. The weld 402 can secure the inner fixation element 218 relative to the cup 516 in a particular orientation. More particularly, the weld 402 can resist relative rotation between the inner fixation element 218 and the cup 516 such that an angular distance between the second distal tip 220 and an inner pinch point 404 is established and maintained.

The inner pinch point 404 can be similar to the outer pinch point 328 described above. The inner pinch point 404 can be at a location where the inner fixation element 218 makes first contact with a distal cup end 406 along the helix 302. For example, the inner pinch point 404 may be at a location between the inner fixation element 218 and the cup 516 at the location where the components converge. Tissue is stopped and pinched at the inner pinch point 404 when the inner fixation element 218 is screwed into the target tissue.

In an embodiment, the inner pinch point 404 is at the weld 402 or at another location between an inner edge of the distal cup end 406 and an outer surface of the inner fixation element 218. Like the outer pinch point 328, the inner pinch point 404 may be at a predetermined angular separation from the second distal end. For example, whereas the outer pinch point 328 may be 1.5 turns from the first distal end, the inner pinch point 404 can be 1.5 turns or more from the second distal end along the inner helix 302 (shown as 1.75 turns in FIG. 4).

It can be desirable for the outer pinch point 328 to engage the target tissue before the inner pinch point 404 engages the tissue. The outer fixation element 212 can have a primary purpose of securing the biostimulator 100 to the target tissue, and the inner fixation element 218 can have a primary purpose of acting as an electrode to electrically communicate with the target tissue. Thus, it may be preferable that the pinch point (which enhances retention of the tissue) be at the outer fixation element 212 to grip the tissue. To that end, the outer pinch point 328 may be more distal than the inner pinch point 404. For example, the inner pinch point 404 may be 1.75 turns from the second distal tip 220, whereas the outer pinch point 328 maybe 1.5 turns from the first distal tip 216. Accordingly, when the fixation elements 106 pierce the target tissue at the same time, the biostimulator 100 can be rotated until the target tissue is pinched at the outer pinch point 328. In such a position, the target tissue may be distal to the inner pinch point 404, e.g., by 0.25 turns. Thus, the likelihood of the inner fixation element 218 causing tissue trauma can be reduced by changing the pinch point locations.

A location of the second distal tip 220 and/or the weld 402 relative to the flange 214 of the housing 206 may be controlled. In an embodiment, an inner alignment marker 410 may be located on a distal hub 412 of the flange 214. The distal hub 412 can extend distally from a distal-facing surface of the flange 214 such as a distal shoulder surface 420 extending transverse to the longitudinal axis 208 distal to a flange shoulder 460. The alignment marker 410 can be a notch machined or pressed into the distal hub 412 at a predetermined location. For example, the flange 214 may include a plurality of interrupted external threads 414, the function of which is described further below, and the inner alignment marker 410 may be circumferentially aligned with one of the interrupted external threaded segments. The second distal tip 220 of the inner fixation element 218 may be oriented to the inner alignment marker 410. More particularly, a vertical plane containing the longitudinal axis 208 and passing through the inner alignment marker 410 may also contain the second distal tip 220. In other words, the second distal tip 220 can be radially aligned with the inner alignment marker 410. When the second distal tip 220 is oriented to the inner alignment marker 410, e.g., within an angular range of the machined notch in the feedthrough, the weld 402 may be formed between the inner fixation element 218 and the cup 516. Thus, a relative orientation between the inner fixation element 218 and both the cup 516 and the flange 214 can be set.

Referring to FIG. 5, a cross-sectional view of a distal portion of a biostimulator having coaxial fixation elements is shown in accordance with an embodiment. The relative stiffnesses of fixation elements 106 can depend on a geometry of the elements. In an embodiment, a first pitch 502 of the outer helix 304 is equal to or less than a second pitch 504 of the inner helix 302. For example, the pitch of the inner fixation element 218 may be nominally 0.040-inch, and the pitch of the outer fixation element 212 may be equal to or less than 0.040-inch. Equal pitches of the fixation elements 106 can cause the fixation elements 106 to advance into the target tissue at a same or similar rate. By way of example, the pitches can vary within a range of 0.010-inch to 0.200-inch, e.g., between 0.020-inch to 0.100 inch. In some embodiments, the first pitch 502 can be greater than the second pitch 504.

Other geometric characteristics that can affect stiffness of the fixation elements 106 includes a cross-sectional dimension of the fixation element wires. In an embodiment, the outer fixation element 212 has a wire diameter in a range of 0.010-inch to 0.030-inch, e.g., 0.016-inch. A wire diameter of the inner fixation element 218 may be less than the wire diameter of the outer fixation element 212. For example, the inner fixation element 218 can have a wire diameter in a range of 0.005-inch to 0.020-inch, e.g., 0.011-inch. Accordingly, each characteristic of the fixation elements 106 may not individually promote a lower stiffness of the outer fixation element 212, but rather, a combination of all of the characteristics may result in such relative stiffness.

The biostimulator 100 can include the helix mount 321, which can be mounted on the housing 206. For example, the helix mount 321 can have an internal thread that mounts on an external thread of the flange 214 by a threaded connection 508. Alternatively, an inner surface of the helix mount 321 can be cylindrically shaped and similar to an outer surface of the flange 214 such that the helix mount 321 can be press fit onto the flange 214 at a press fit connection 510. Both connection types are illustrated in FIG. 5 for brevity. It will be appreciated, however, that the biostimulator 100 may have only one of the connection types circumferentially around the helix mount 321. In an embodiment in which the inner surface of the helix mount 321 is wider than the outer surface of the flange 214, a spot weld 512 or heat stake may be used to bond the helix mount 321 to the flange 214. Similarly, the helix mount 321 and the flange 214 can be connected by ultrasonic staking or mechanical interlock features.

The coaxial fixation elements 106 may pull tissue inward when the biostimulator 100 is screwed into the target site. More particularly, the helix mount 321 can include a central opening 514 that extends along the longitudinal axis 208, and the fixation elements 106 can pull the tissue into the central opening 514. For example, the inner fixation element 218 can extend through the central opening 514 from the cup 516 of the biostimulator 100 to the second distal tip 220. As the inner fixation element 218 is screwed into the target tissue, the target tissue can move proximally along the helical element into the central opening 514 toward the cup 516.

To facilitate tissue capture within the central opening 514 of the helix mount 321, the central opening 514 can have a tapered profile. The central opening 514 can widen from a proximal edge 518 to a distal edge 520 of the helix mount 321. More particularly, the distal dimension of the central opening 514 can be greater than a proximal dimension of the central opening 514. In an embodiment, the helix mount 321 includes a chamfer surface 522 that extends from the proximal edge 518 to the distal edge 520. The chamfer surface 522 is essentially a frustoconical surface that tapers proximally inward from the distal edge 520 of the helix mount 321. Accordingly, the chamfer surface 522 provides a funnel to receive and guide the target tissue inward toward the cup 516.

In an embodiment, the biostimulator 100, and more particularly the cup 516, can contain a filler 530. The filler 530 can be referred to as a monolithic controlled release device (MCRD). The MCRD can include a therapeutic material and can be loaded into the cup 516. The therapeutic agent can include a corticosteroid, such as dexamethasone sodium phosphate, dexamethasone acetate, etc. Furthermore, the therapeutic agent can be loaded in a silicone matrix. Accordingly, the filler 530 can deliver a specified dose of a therapeutic agent, e.g., a corticosteroid, into the target tissue. When the target tissue is drawn into the central opening 514 by the coaxial fixation elements and guided toward the cup 516, the therapeutic agent can be effectively delivered into the tissue after the biostimulator 100 is implanted in a patient. Accordingly, inflammation or injury of the captured tissue may be reduced.

The filler 530 can be contained in an electrode cavity 532 of the cup 516. For example, the cup 516 can include an electrode wall 534 extending distally from an electrode base 536. The electrode wall 534 can extend around the electrode cavity 532 to surround the filler 530 and separate the filler 530 from an insulator 570 or the flange 214 that is radially between the cup 516 and the flange 214. The electrode cavity 532 can be located on the longitudinal axis 208. A pin 538 of the cup 516 can extend proximally from the electrode base 536 along the longitudinal axis 208 through the insulator 570. The pin 538 can receive pacing impulses from circuitry within the electronics compartment 210 and transmit the electrical signals to the inner fixation element 218, which can act as a portion of the distal electrode 202 to deliver the pacing impulses to the captured tissue.

In an embodiment, the inner fixation element 218 is mounted on the cup 516 radially inward from the outer fixation element 212, which is mounted on the helix mount 321. Alternatively, the inner fixation element 218 can be mounted on a shaft (not shown). The electrode cavity 532 can extend proximally from a distal cup end 406 of the cup 516 to a depth. More particularly, the electrode cavity 532 can have a bottom that coincides with a distal surface of the electrode base 536. The electrode cavity 532 can be divided into portions based on a structure of the electrode wall 534. More particularly, the electrode cavity 532 can include a distal counterbore 540 that enlarges a proximal cavity 542 of the electrode cavity 532. The filler 530 can be placed in the proximal cavity 542, and thus, can be located proximal to the distal counterbore 540.

An inner surface of the electrode wall 534 that defines the electrode cavity 532 can have a ledge 546 extending between the proximal cavity 542 and the distal counterbore 540. The proximal cavity 542 can be coaxial with the distal counterbore 540, however, the cavity portions have different inner diameters, and thus, the ledge 546 is a transverse surface extending radially outward. Accordingly, the ledge 546 can form a shelf to receive the inner fixation element 218 when it is inserted into the cup 516.

The inner fixation element 218 can be mounted on the ledge 546 of the distal counterbore 540. More particularly, a proximal end 548 of the inner fixation element 218 can be mounted on the ledge 546. A vertical location of the ledge 546 relative to the flange 214 may be controlled. For example, a longitudinal offset between the ledge 546 and a distal shoulder surface 547 may be predetermined during assembly of the feedthrough to the flange 214. When the inner fixation element 218 is inserted into the cup 516, it can bottom out on the ledge 546. More particularly, a proximal end 548 of the inner fixation element 218 can be coincident with the ledge 546. Thus, given that a length of the inner fixation element 218 is known, a longitudinal offset between the second distal tip 220 and the distal shoulder surface 547 can also be predetermined. That is, the counterbored shelf can provide helix height control for the inner fixation element 218.

An outer diameter of the wire coil forming the inner fixation element 218 can be similar to an inner diameter of the distal counterbore 540. More particularly, the outer diameter of the wire coil can be sized to form a slip or interference fit between the inner fixation element 218 and the electrode wall 534. Accordingly, the inner fixation element 218 can be secured within the distal counterbore 540. The secured fit can allow for good weld contact during attachment of the inner fixation element 218 to the cup 516, as described above, and can provide moment support. More particularly, the slip or interference fit can reduce the likelihood of the inner fixation element 218 pivoting about the weld 402 within the cup 516. Thus, fatigue stresses at the weld 402 can be reduced by the closely matched wire coil diameter and inner diameter of the distal counterbore 540 to enhance fatigue resistance of the biostimulator 100 when implanted in pulsating tissue.

In addition to engaging the target tissue and acting as an electrode, the inner fixation element 218 can retain the filler 530 within the proximal cavity 542 of the cup 516. In an embodiment, the inner fixation element 218 blocks the filler 530 from dislodging from the cup 516. For example, the filler 530 can have a filler dimension 550, e.g., a maximum cross-sectional dimension taken transverse to the longitudinal axis 208, that is greater than an inner dimension 552 of the inner fixation element 218, e.g., an inner diameter of the wire coil forming the fixation element 106. Such a relative size prevents the filler 530 from passing through the inner diameter of the wire coil, and thus, promotes retention of the filler 530 within the cup 516. Furthermore, the inner dimension 552 of the inner fixation element 218 can be sized to allow a maximum area of the filler 530 to be exposed to a surrounding environment through the interior space of the wire coil. Accordingly, drug can consistently elute from the filler 530 through the lumen of the inner fixation element 218 lumen toward the target tissue for reliable and predictable therapy.

Figure 6A:
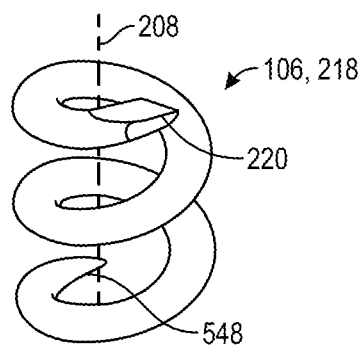
FIGS. 6A-6C are various views of an inner fixation element, in accordance with an embodiment.

Referring to FIG. 6A, a perspective view of an inner fixation element is shown in accordance with an embodiment. As shown in FIG. 5 and in FIG. 6A the proximal end 548 of the inner fixation element 218 can be a flat surface. For example, the proximal end 548 can be ground flat such that a surface of the proximal end 548 forms a plane that is orthogonal to the longitudinal axis 208. The flat surface allows the inner fixation element 218 to be seated on the ledge 546 of the cup 516.

At least a portion of one or more of the outer fixation element 212 or the inner fixation element 218 may be formed from a biodegradable material. By way of example, the inner fixation element 218 may be entirely formed of a metal that biodegrades, either through bulk or surface erosion, when implanted within the patient. Alternatively, the outer fixation element 212 may be partly or entirely formed from a biodegradable material, e.g., a biodegradable metal such as iron or magnesium.

Figure 6B:
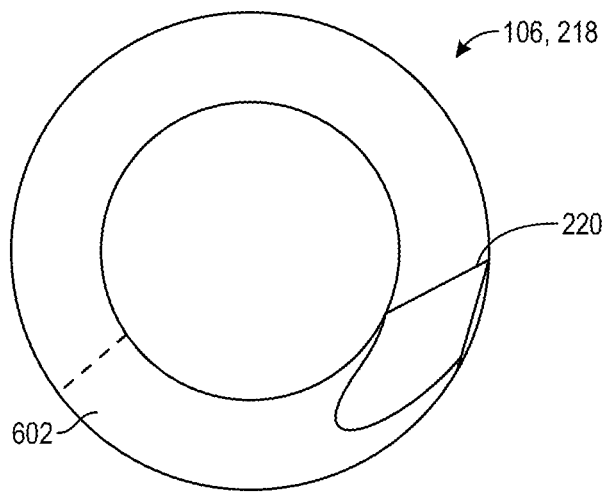

Referring to FIG. 6B, an end view of an inner fixation element is shown in accordance with an embodiment. Only a portion of the fixation elements 106 may be biodegradable. For example, a distal end of the inner fixation element 218 near the second distal tip 220 may be a degradable portion 602 (shown distal to the dotted line). The portion of the inner fixation element 218 that is proximal to the degradable portion can be a same or different material. For example, the non-degradable portion may include a core of degradable material jacketed by a layer of nondegradable material. The outer fixation element 212 may have a similar composite structure.

Figure 6C:
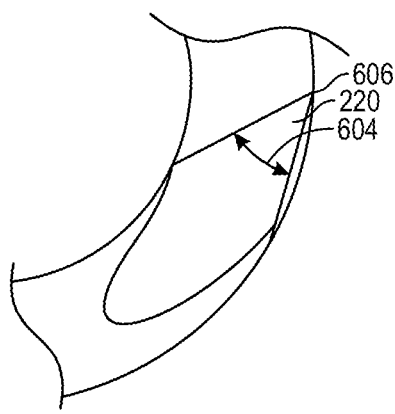

Referring to FIG. 6C, a detailed view of an inner fixation element is shown in accordance with an embodiment. Dimensional characteristics of the distal tips of the coaxial fixation elements 106 can be shaped to facilitate penetration of the target tissue. By way of example, the second distal tip 220 can have a bevel angle 604 in a range of 30 to 60 degrees, e.g., 47 degrees, that narrows to a sharpened piercing tip 606. It will be appreciated that the illustrated geometry can also be found in the outer fixation element 212.

Figure 7A:
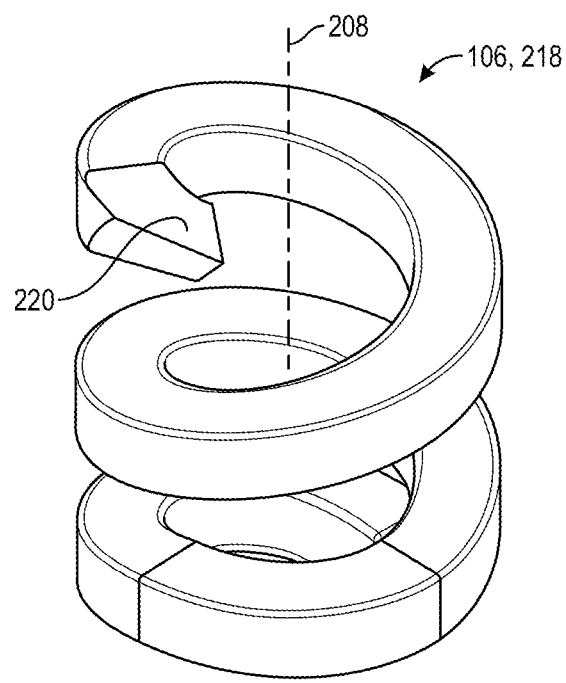
FIGS. 7A-7B are various views of an inner fixation element, in accordance with an embodiment.

Referring to FIG. 7A, a perspective view of an inner fixation element is shown in accordance with an embodiment. The inner fixation element 218 may be a tube-cut fixation element 106. More particularly, the fixation element 106 can be formed from a cylindrical tube, such as a piece of hypotube. The wire coil of the fixation element 106 is formed from the wall of the cylindrical tube. In an embodiment, the cylindrical tube is used in a laser cutting process. That is, an Nd:YAG laser, or another laser type, can be used to cut a profile into a sidewall of the cylindrical tube. The profile can be a helical gap that forms the helical relief of the inner fixation element 218. A similar process may be used to form a tube-cut outer fixation element 212.

A cross-sectional area of a tube-cut fixation element 106 may be non-round. For example, the cross-sectional area taken transverse to the inner helix 302 can be a quadrilateral area, e.g., rectangular. The quadrilateral area can include the inner surface of the tube, the outer surface of the tube, and an upper and lower surface that is formed by the laser cut through the tube wall. Processing can include polishing processes, such as deburring, electropolishing, etc. to form the tube-cut fixation element 106 that can be used as an outer or inner fixation element 106.

Figure 7B:
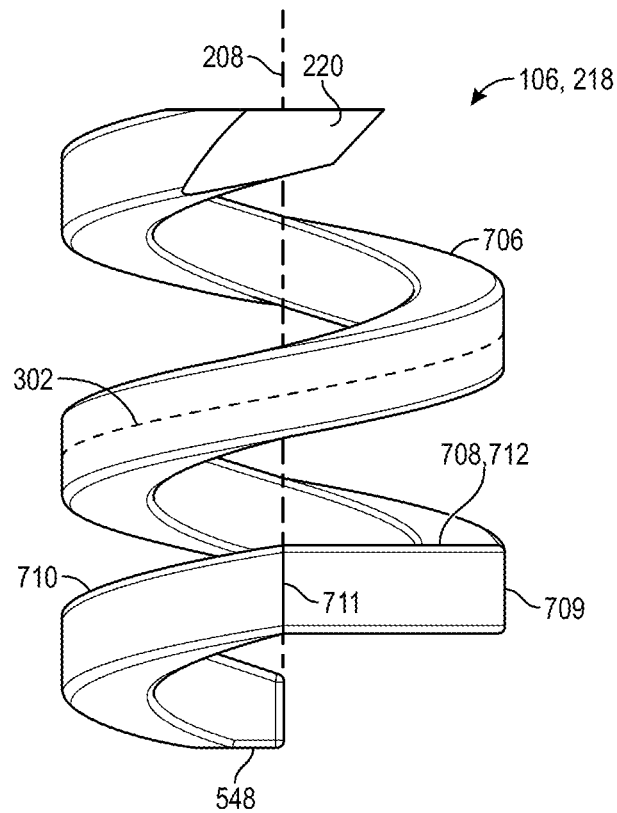

Referring to FIG. 7B, a side view of an inner fixation element is shown in accordance with an embodiment. The laser cutting process used to form the inner fixation element 218 from tubular stock can have a higher precision than other forming processes, such as wire winding. The high precision of the laser cutting process allows for more complex geometries to be incorporated into the inner fixation element 218. More particularly, a profile of the inner fixation element 218 can incorporate profile segments that are non-helical. In an embodiment, the inner fixation element 218 has a helical coil section 706 and a flat coil section 708.

A helical coil section 706 can be a section of the inner fixation element 218 that extends along a helical axis, e.g., the inner helix 302. The helical coil section 706 can extend proximally from the second distal tip 220 to a distal terminus 709 of the flat coil section 708. Similarly, a second helical coil section 710 can be located proximal to the flat coil section 708. More particularly, the flat coil section 708 can be intermediate between the helical coil section 706 and the second helical coil section 710. The second helical coil section 710 can extend proximally from a proximal terminus 711 of the flat coil section 708.

The flat coil section 708 can be a small, flat section that extends around the longitudinal axis 208 over an angle of one turn or less. The flat section can extend circumferentially instead of helically. The flat coil section 708 has a distal facing surface 712 that extends along a plane transverse to the longitudinal axis 208. In an embodiment, the distal facing surface 712 of the flat coil section 708 provides an area for the inner fixation element 218 to be welded to the cup 516. To facilitate welding, a vertical offset between the distal facing surface 712 of the flat coil section 708 and the flat proximal end 548 of the inner fixation element 218 can be equal to a vertical offset between the ledge 546 and the distal cup end 406. More particularly, when the inner fixation element 218 is inserted into the cup 516, the distal facing surface 712 of the flat coil section 708 may be aligned to and/or coplanar with the distal cup end 406 of the cup 516. The coplanar surfaces provide a target for a laser beam to be directed at during the welding process. Furthermore, given that the distal cup end 406 and the distal facing surface 712 of the flat coil section 708 are both flat, the laser beam can be more easily directed at the interface between the components, and thus, the risk of rejection due to missed welds may be decreased.

It will be appreciated that the tube-cut fixation element 106 can have advantageous characteristics, as compared to a coiled round wire. For example, the quadrilateral cross-sectional area may increase a stiffness of the fixation element 106, allowing it to more easily pierce the target tissue during anchoring. Furthermore, the quadrilateral cross-sectional area may completely fill the helical gap of the helix mount flange 322. The filled gap may provide a cylindrical outer surface of the header assembly 320 that is smoother and has fewer edges exposed to tissue during delivery and implantation.

Figure 8:
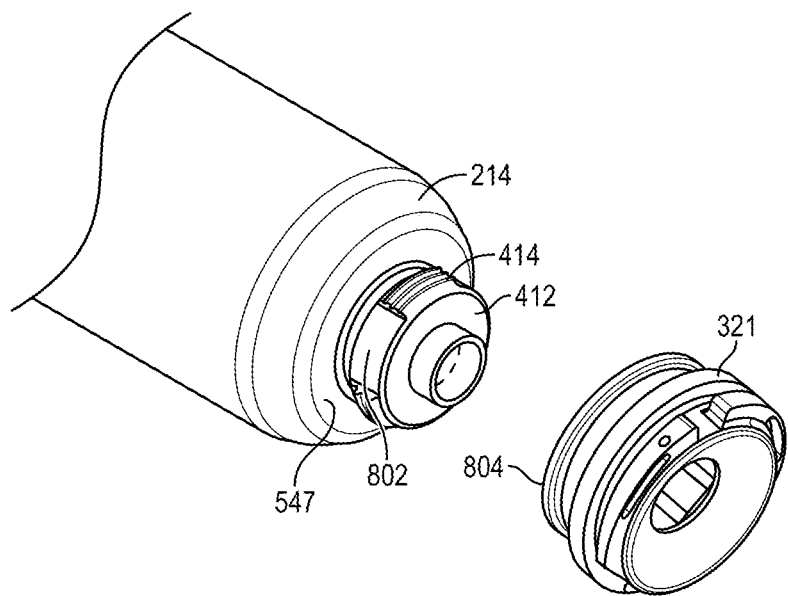
FIG. 8 is a perspective exploded view of a helix mount being installed on a housing of a biostimulator, in accordance with an embodiment.

Referring to FIG. 8, a perspective exploded view of a helix mount being installed on a housing of a biostimulator is shown in accordance with an embodiment. As described above, the flange 214 of the biostimulator 100 can have interrupted external threads 414. The interrupted thread design of the biostimulator 100 allows for orientation control. More particularly, as described below, the interrupted threads allow for the helix mount 321 to be inserted onto the distal hub 412 of the flange 214 at a predetermined orientation prior to rotating the helix mount 321 to secure the helix mount 321 to the interrupted threads 414.

Interrupted external threads 414 can include several threaded segments distributed about the distal hub 412 of the flange 214. The threaded segments can be machined on the distal hub 412, which may be titanium. More particularly, fully helical threads can be formed on the distal hub 412, e.g., using a thread cutting die, and then longitudinal slots can be formed through the threads to interrupt the helical threads and form the threaded segments. The longitudinal slots can be thread interruptions 802. Each threaded segment can extend over a respective circumferential width (an angular distance measured about the longitudinal axis 208), and can be separated from one or more adjacent threaded segments by the thread interruptions 802. The thread interruptions 802 can be a radially outward surface of the distal hub 412 having a smaller diameter than the threaded segments. For example, a diameter of thread interruptions 802 can be less than or equal to a minor diameter of the threaded segments of helix mount 321.

As described below, the threaded segments can be distributed in such a manner that they form keys that fit within slots of the helix mount 321. Accordingly, the helix mount 321 can be inserted over the distal hub 412 of the flange 214 until a proximalmost surface 804 of the helix mount 321 contacts the distal shoulder surface 547. When the helix mount 321 is inserted over the distal hub 412 and dropped into place, proximalmost surface 804 can bottom out on, and be apposed to, the distal shoulder surface 547 of the flange 214.

Figure 9:
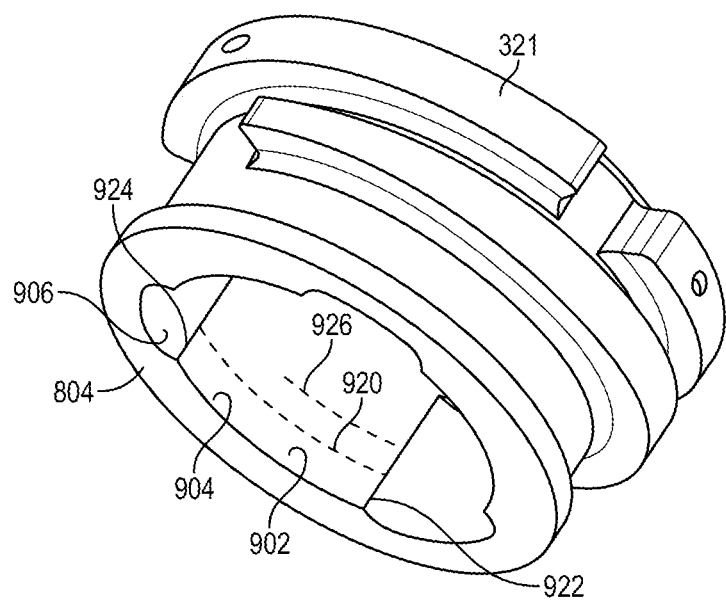
FIG. 9 is a perspective view of a helix mount, in accordance with an embodiment.

Referring to FIG. 9, a perspective view of a helix mount is shown in accordance with an embodiment. The proximal view of the helix mount 321 reveals an inner surface 902 of the helix mount 321, within an interior of the helix mount 321. The inner surface 902 of the helix mount 321 can be a threadless, e.g., cylindrical, surface. The helix mount 321 can be fabricated from a polymer, e.g., polyether ether ketone (PEEK). Accordingly, the interrupted external threads 414, which may be titanium, can be formed from a harder material than the inner surface 902 of the helix mount 321.

The inner surface 902 of the helix mount 321 can extend along the interior surfaces of one or more blanks 904 and one or more slots 906. The slots 906 can be radially offset from the longitudinal axis 208 by a greater distance than the blanks 904. Furthermore, the slots 906 can have circumferential widths and be distributed about the inner surface 902 at angles that match the pattern of the interrupted external threads 414 on the distal hub 412 of the flange 214. Accordingly, the slots 906 can receive the interrupted external threads 414 when the helix mount 321 is dropped into place over the distal hub 412 of the flange 214. Similarly, the blanks 904 of the helix mount 321 can be received within thread interruptions 802 of the distal hub 412 that have matching circumferential widths and distributions. In other words, a cross-sectional profile of the inner surface 902 of the helix mount 321 can match a cross-sectional profile of the distal hub 412 of the flange 214 such that the helix mount 321 fits over the flange 214.

Given that the blanks 904 are raised relative to the slots 906, the inner surface 902 of the helix mount 321 can include an interrupted thread design when threads are cut into the blanks 904. For example, when the interrupted external threads 414 cut into the inner surface 902 of the helix mount 321, interrupted internal threads can be formed on the inner surface 902 of the helix mount 321. Similarly, when threads are pre-formed in the inner surface 902 of the helix mount 321, e.g., prior to connecting the helix mount 321 to the flange 214, the helix mount 321 has interrupted internal threads (not shown) that include depressed wells to allow the header mount to slip over the interrupted external threads 414 of the flange 214 prior to being rotated into place.

Figure 10A:
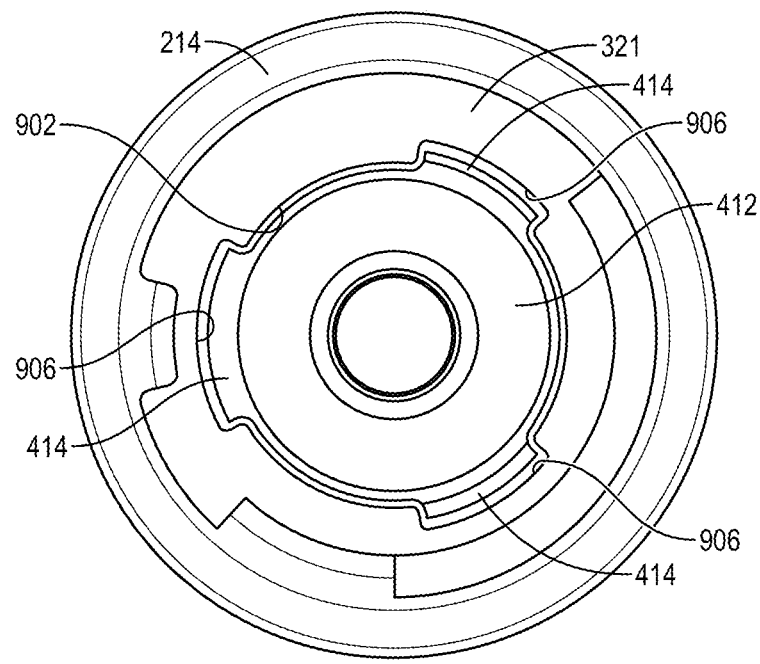
FIGS. 10A-10B are top views of a helix mount being installed on a flange of a housing, in accordance with an embodiment.

Referring to FIG. 10A, a top view of a helix mount being installed on a flange of a housing is shown in accordance with an embodiment. When the helix mount 321 is dropped into place over the distal hub 412 of the flange 214, the interrupted external threads 414 can fit within the slots 906. In an initial configuration, e.g., prior to turning the helix mount 321 to a final configuration, the interrupted external threads 414 are not engaged with the inner surface 902 of the helix mount 321. In the top-down cross-sectional view of FIG. 10A, it is apparent that the interrupted external threads 414 may be arranged to allow for assembly of the helix mount 321 to the flange 214 in only one rotational orientation. More particularly, an angular width of at least one of the threaded segments may be greater than one or more of the other threaded segments, and may fit within only one corresponding slot 906. Accordingly, the wider threaded segment must be aligned with the corresponding slot 906 in order to insert the helix mount 321 over the distal hub 412.

Figure 10B:
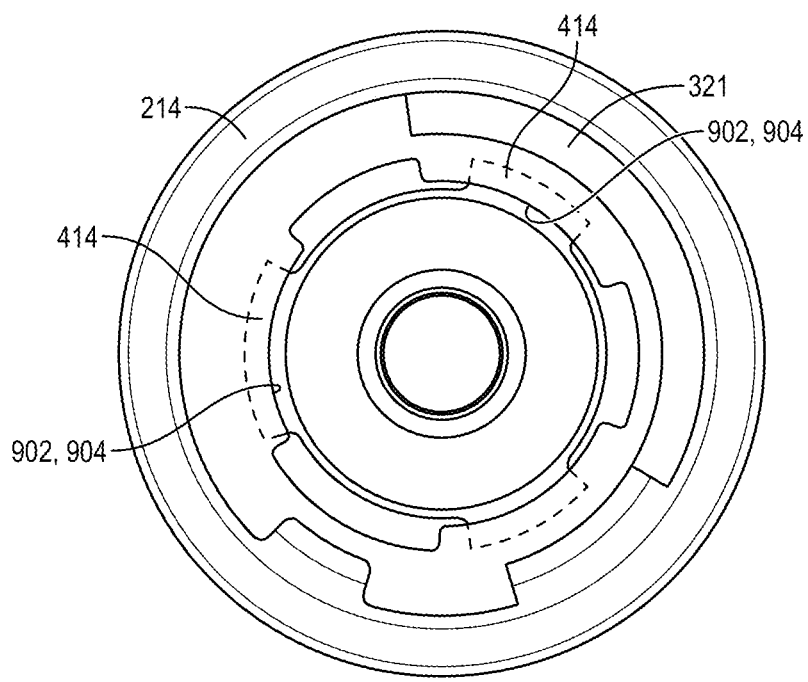

Referring to FIG. 10B, a top view of a helix mount installed on a flange of a housing is shown in accordance with an embodiment. When the helix mount 321 is rotated into the final configuration relative to flange 214, the interrupted external threads 414 can tap into the inner surface 902 of the helix mount 321. The engagement between the interrupted external threads 414 and the inner surface 902 is represented by dotted lines showing that the outer surface of the interrupted external threads 414 is radially outward from the inner surface 902 of the helix mount 321. It will be appreciated that rotation of the helix mount 321 causes the interrupted external threads 414 of the flange 214 to cold form a thread into the helix mount 321. Cold forming the thread can displace material, rather than remove material, from the helix mount 321. Accordingly, a strong and secure joint can be formed between the interrupted external threads 414 and the inner surface 902 of the helix mount 321 within the threaded blanks 904.

Cold forming the threads into the helix mount 321 at the time of assembly represents one manner of securing the helix mount 321 to the flange 214. In an embodiment, however, one or more threads, or partial threads, are formed in the inner surface 902 of the helix mount 321. More particularly, internal threads can be pre-formed in the helix mount 321. Pre-formed internal threads can be cut into the blanks 904 of the helix mount 321 by a thread tap during manufacturing of the helix mount 321. The pre-threaded inner surface 902 can match the external threads of the flange 214. Accordingly, when the helix mount 321 is loaded onto the flange 214, rotation of the helix mount 321 relative to the flange 214 can cause the internal and external threads to mesh such that the components become secured to each other.

Referring again to FIG. 9, in an embodiment, an example pre-threaded full thread 920 is shown as a dotted line (indicating that it can be optionally formed prior to assembling the helix mount 321 to the flange 214). The pre-threaded full thread 920 can extend over an entire arc length of the blank 904, e.g., from a first lateral edge 922 to a second lateral edge 924. The full thread can interface with the threads of the flange 214 such that, when the helix mount 321 is screwed onto the flange 214, there is no cold-working of the inner surface 902 of the helix mount 321 along the pre-threaded full thread 920.

The helix mount 321 can include partial threads pre-threaded into respective blanks 904. In an embodiment, an example pre-threaded partial thread 926 is shown as a dotted line extending over only a portion of the arc length between the first lateral edge 922 and the second lateral edge 924. For example, the full arc length may extend over a 60 degree arc angle, and the partial arc length of the partial thread may extend over a 30 degree angle. The partial thread can fit an external thread of the flange 214, however, when the external thread advances within the internal thread, the end of the internal thread will impede advancement of the helix mount 321. More particularly, to fully engage the blank 904 with the corresponding interrupted external thread of the flange 214, the helix mount 321 can be forced to rotate further, beyond the arc length of the pre-formed partial thread, by cold-forming a thread into the blank 904. Cold-foil ling the thread can extend the partial thread 926 from the termination point of the pre-thread, e.g., at the 30 degree mark, to a location between the termination point and the second lateral edge 924, e.g., to a 50 degree mark. Accordingly, screwing the helix mount 321 onto the flange 214 can initially involve engagement between pre-formed internal and external threads, and subsequently can involve cold-forming threads into the helix mount 321 at the time of assembly.

The use of partial or full pre-formed internal threads can mitigate some assembly risk associated with cold-forming the entire thread into the blanks 904. Cold-forming the threads can be performed blindly, as described above. More particularly, the helix mount 321 can be dropped into place over the flange 214 and rotated to secure the components together. The threads will start into the blanks 904 at any location that that the screwing action begins. Such blind cold-forming, however, runs the risk that the threads will start at a location that is not intended. By contrast, when the internal threads are at least partially pre-formed in the blanks 904, the internal threads and external threads will engage at a predetermined location. That predetermined location is the location at which the pre-threads mesh with each other upon rotation of the helix mount 321 relative to the flange 214. Accordingly, a combination of pre-threads and/or cold-formed threads in the helix mount 321 may be used to achieve accurate positioning between the helix mount 321 and the flange 214, and tight securement of the helix mount 321 to the flange 214.

To mitigate assembly risks, such as potential cross-threading or over-rotation of the helix mount 321 to the flange 214, several assembly techniques can be employed. The assembly techniques can be implemented in manual, semi-automated, or automated assembly processes, and can promote ease of assembling the biostimulator components. For example, assembly tools that provide torque, force, alignment, or other feedback for an operator or a computer can be used. The tools may include, e.g., optical feedback, to provide feedback that can be used to confirm proper assembly between the helix mount 321 and the flange 214. In an embodiment, the assembly is performed robotically. For example, a robot can place the helix mount 321 onto the flange 214 and rotate the components to secure the components to each other. The robot can include one or more processors configured to execute instructions stored on a non-transitory computer readable medium to cause the robot to assemble the biostimulator components. The instructions may, for example, include guard bands in one or more mechanical assembly variables to ensure that the components are assembled correctly. For example, the robot may assemble the components according to a rotation parameter of the instructions, which causes the robot to screw the helix mount 321 onto the flange 214 over a predetermined angle. The guard band can include a margin of error in the angular rotation. When the robot detects, via one or more sensors, that rotation is within the margin of error, then the biostimulator 100 can pass inspection. When the robot detects, via the one or more sensors, that rotation exceeded the margin of error, then biostimulator 100 can be rejected and/or reworked to meet design specifications.

Rotation of the helix mount 321 relative to the flange 214 can be controlled to achieve a predetermined orientation between one or more of the distal tips of the fixation elements 106 or the pinch points of the fixation elements 106. For example, rotation of the helix mount 321 to engage the interrupted external threads 414 into the plastic of the helix mount 321 may be controlled mechanically, electronically, or otherwise. Mechanical control may be achieved using a tool having a rotational stop that limits rotation of the helix mount 321 relative to the flange 214. Electronic control can be achieved, for example, by a stepper motor that moves the helix mount 321 from the initial configuration to the final configuration. The stepper motor can be part of the robot described above. Rotation can also be controlled manually, e.g., by rotating the helix mount 321 until an operator visually identifies that the inner fixation element 218 is at a predetermined orientation relative to the flange notch 326 or another helix mount datum. For example, the operator can rotate the helix mount 321 until the second distal tip 220 is circumferentially aligned with the flange notch 326. By way of example, rotation of the helix mount 321 from the initial configuration to the final configuration may be through an angle of 60 degrees, or any other angle that achieves the predetermined rotational orientation between the distal tips 216, 220 and/or pinch points 328, 404.

Figure 11:
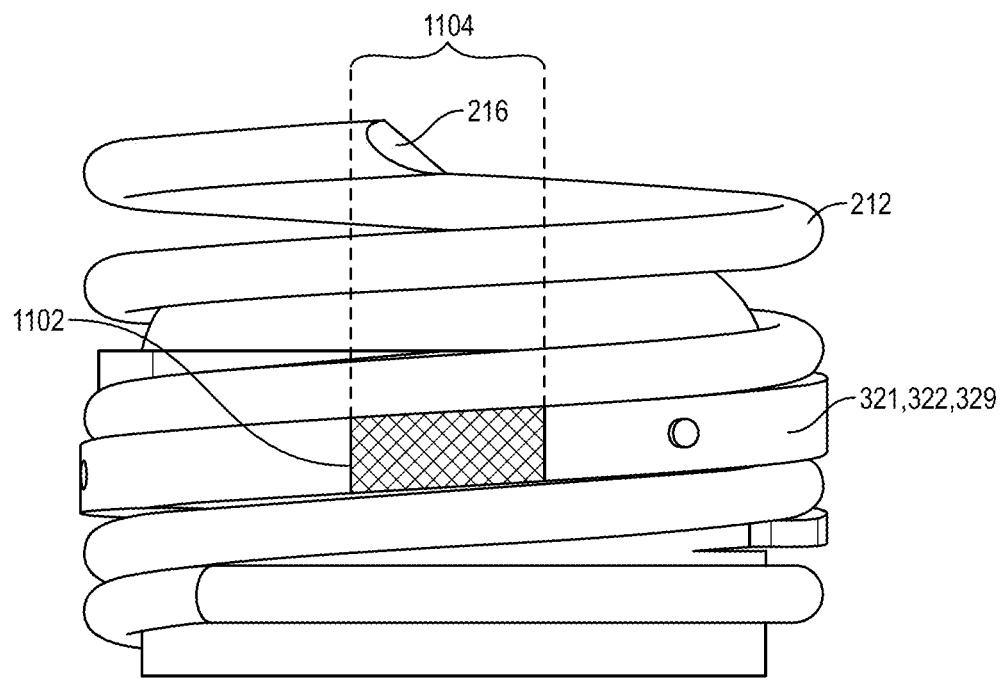
FIG. 11 is a side view of a header assembly having an additive alignment marker, in accordance with an embodiment.

Referring to FIG. 11, a side view of a header assembly having an additive alignment marker is shown in accordance with an embodiment. The helix mount 321 can include an outer alignment marker 1102 to define a range within which a leading point of the first distal tip 216 can be aligned to set a predefined clocking of the outer fixation element 212 on the biostimulator 100. For example, the outer alignment marker 1102 can be a laser mark, a printed stripe, or another additive feature that is visually recognizable by an assembler. The outer alignment marker 1102 can define an alignment range 1104, e.g., a circumferential range, measured along the circumference or outer surface of the helix mount flange 322. The alignment range 1104 can be between a leftward boundary and a rightward boundary of the outer alignment mark.

Figure 12:
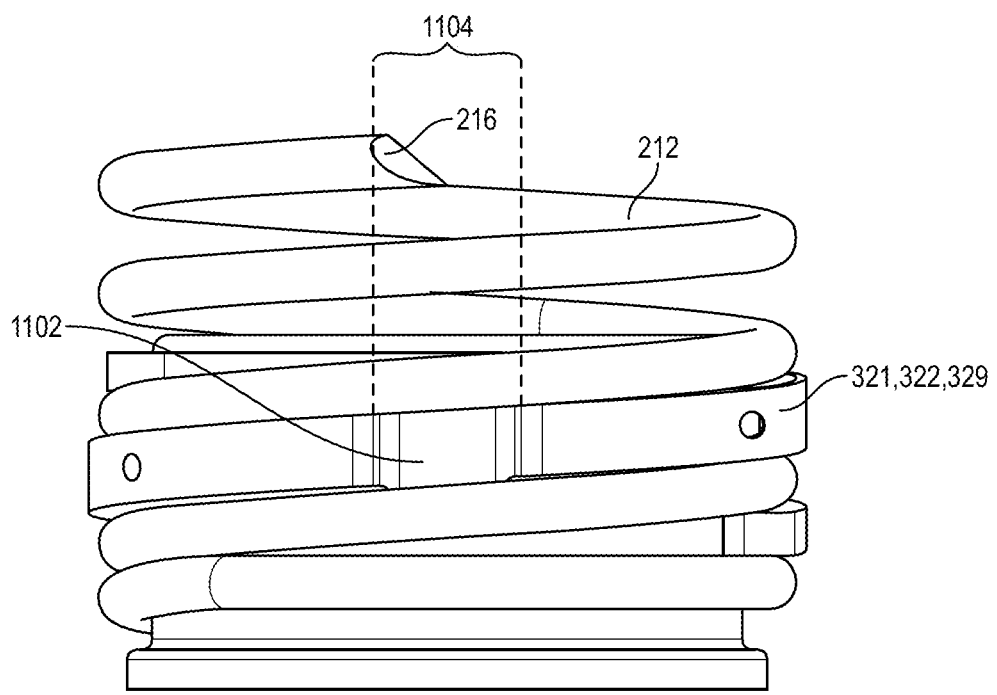
FIG. 12 is a side view of a header assembly having a reductive alignment marker, in accordance with an embodiment.

Referring to FIG. 12, a side view of a header assembly having a reductive alignment marker is shown in accordance with an embodiment. In an alternative embodiment, the alignment range 1104 can be defined by a notch that forms the outer alignment marker 1102. The notch can be a groove formed in the helix mount flange 322, e.g., by machining. The outer alignment marker 1102 may also be formed using another reductive process, such as etching. It will be appreciated that, whether the outer alignment marker 1102 is formed by an additive or reductive process, the marker can define the alignment range 1104 within which the first distal tip 216 may be placed to ensure a predetermined rotational orientation between the outer fixation element 212 and the helix mount 321.

The alignment marker is described above, e.g., the outer alignment marker 1102 and the inner alignment marker 410, each have predetermined relationships relative to the respective distal tips. More particularly, the outer alignment marker 1102 can be aligned to the first distal tip 216, and the inner alignment marker 410 can be aligned to the second distal tip 220. Also discussed above is the relative orientation between the distal tips and the respective pinch points. More particularly, the first distal tip 216 can have a predetermined angular separation relative to the outer pinch point 328, and the second distal tip 220 can have a predetermined angular separation relative to the inner pinch point 404. Accordingly, it will be appreciated that a predetermined separation between the inner and outer pinch points 404, 328 can be achieved by setting a separation between the distal tips to the predetermined separation. For example, by separating the first distal tip 216 from the second distal tip 220 by 180 degrees, the outer pinch point 328 can be separated from the inner pinch point 404 by 90 degrees (when the first distal tip-to-outer pinch point separation is 1.5 turns and the second distal tip-to-inner pinch point separation is 1.75 turns).

Relative rotational orientation between the distal tips can also be achieved by a predetermined rotational orientation between the inner surface profile of the helix mount 321 and the outer alignment marker 1102. More particularly, a location of the keyhole pattern of the helix mount 321 can be controlled to the first distal tip 216 to ensure that when the helix mount 321 is placed over the distal hub 412 of the flange 214 and rotated into place, the first distal tip 216 will have the desired angular separation from the second distal tip 220.

Figure 13:
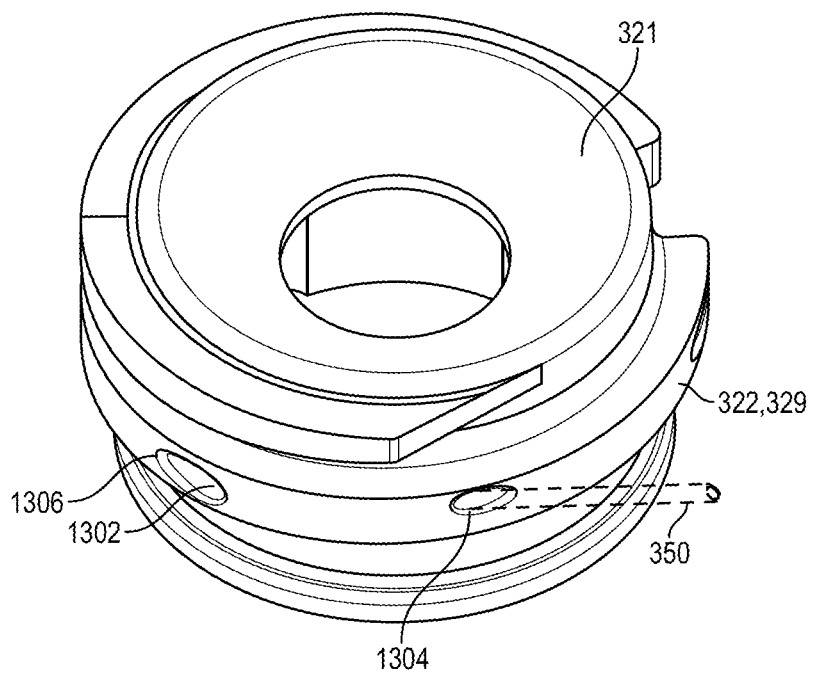
FIG. 13 is a perspective view of a helix mount, in accordance with an embodiment.

Referring to FIG. 13, a perspective view of a helix mount is shown in accordance with an embodiment. Biostimulator 100 may include secondary fixation elements 350. e.g., laterally extending sutures, as shown for example in FIG. 3 above. The secondary fixation elements 350 are shown in phantom in FIG. 13. In an embodiment, the secondary fixation elements 350 are secured within a secondary fixation channel 1302 that extends through the helix mount flange 322. For example, a secondary fixation channel 1302 can extend from a first opening 1304 to a second opening 1306. Both openings can be on the radially outward surface 329 of the helix mount flange 322. Thus, secondary fixation channel 1302 can extend through the helix mount flange 322 and/or the helix mount body 324 in line with the helical path of the helix mount flange 322.

Figure 14:
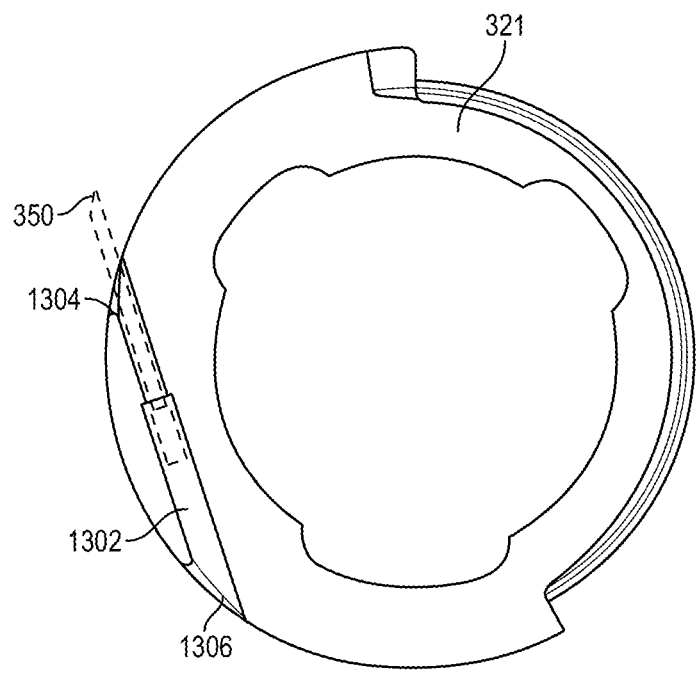
FIG. 14 is a cross-sectional view of a helix mount, in accordance with an embodiment.

Referring to FIG. 14, a cross-sectional view of a helix mount is shown in accordance with an embodiment. The secondary fixation channel 1302 can extend straight between the first opening 1304 and the second opening 1306. The secondary fixation element 350 can be inserted through either of the openings along the secondary fixation channel 1302. For example, an end of a polymeric suture can be inserted through the first opening 1304. The suture can be advanced until the end passes through the second opening 1306 and is exposed to the assembler. The end of the secondary fixation element 350 can be widened, e.g., via heat staking. By heat staking the end, the suture can be deformed to increase a cross-sectional dimension of the suture at the end. In an embodiment, secondary fixation channel 1302 is counterbored. Similarly, a diameter of the first opening 1304 may be less than a diameter of the second opening 1306. More particularly, a dimension of a channel segment extending from the first opening 1304 inward into the helix mount flange 322 and/or the helix mount body 324 may be less than a dimension of the channel extending inward from the second opening 1306. Accordingly, after heat staking, the end of the suture can be pulled back into the secondary fixation channel 1302 through the segment extending from the second opening 1306. As the heat staked end reaches a transition between the channel segments, e.g., at a base of the counterbore, the increased dimension of the suture will resist further movement toward the first opening 1304. Thus, the secondary fixation element 350 can be retained within the secondary fixation channel 1302. A first end of the secondary fixation element 350 can remain within the channel, and a second end of the secondary fixation element 350 may be exposed radially outward from the helix mount 321 to engage target tissue.

Figure 15:
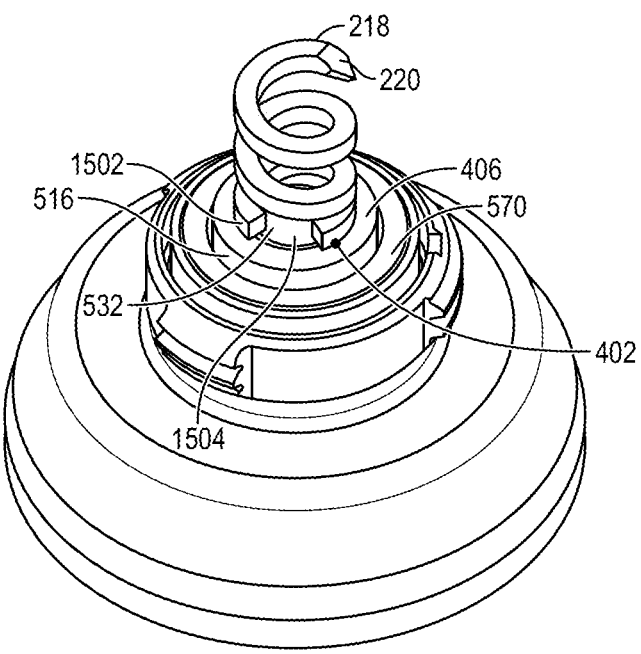
FIG. 15 is a perspective view of a distal portion of a biostimulator having a removed header assembly, in accordance with an embodiment.

Referring to FIG. 15, a perspective view of a distal portion of a biostimulator having a removed header assembly is shown in accordance with an embodiment. The inner fixation element 218 can have an outer diameter that is larger than the distal counterbore 540 and/or an inner diameter of the cup 516. In an embodiment, a proximal turn 1502 of the inner fixation element 218 may not fit within the cup 516. Accordingly, rather than sliding the inner fixation element 218 into the cup 516 and forming the weld 402 at or near the pinch point, the proximal turn 1502 of the inner fixation element 218 may be joined to the distal cup end 406 by a butt weld 402. The butt weld 402 can be formed at the interface of the proximal turn 1502 and the distal cup end 406. The inner fixation element 218 can extend along the inner helix 302 from the proximal turn 1502 to the second distal tip 220.

In an embodiment, a turn notch 1504 may be cut or otherwise formed in the proximal turn 1502. The turn notch 1504 can be an interruption or a discontinuity in the proximal turn 1502 that provides a lateral entry between the electrode cavity 532 and the surrounding environment. The lateral entry can ensure that the MCRD does not swell and choke itself off. More particularly, as the MCRD swells, the lateral entry provides an area for the filler 530 to swell into. Accordingly, the MCRD can release therapeutic agent through the lateral entry, if needed, into the target tissue.

Figure 16:
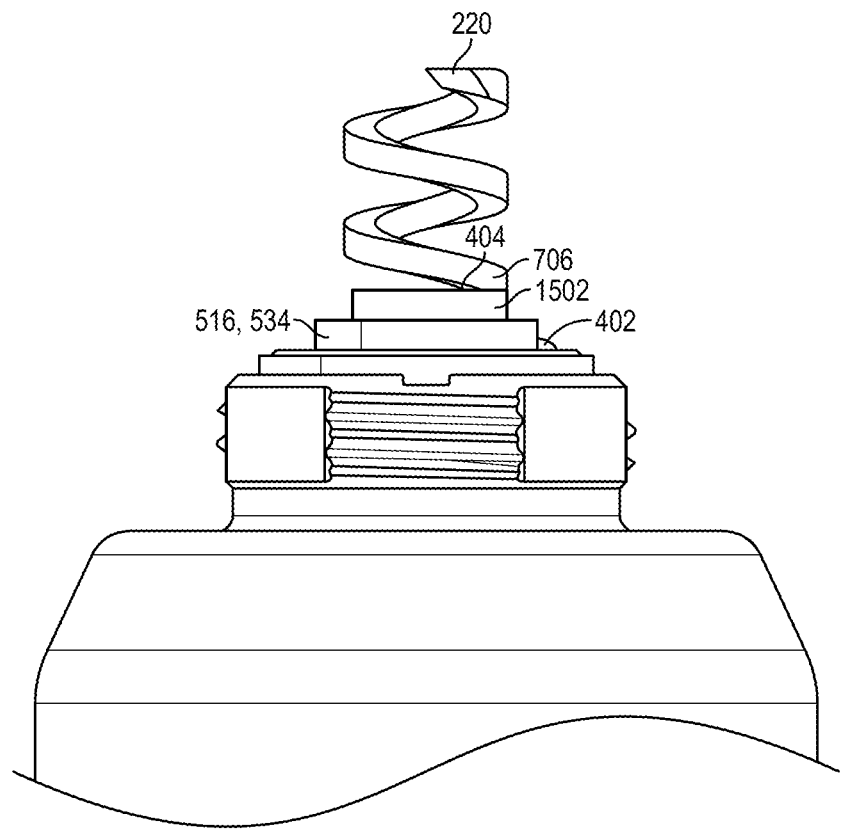
FIG. 16 is a side view of a distal portion of a biostimulator having a removed header assembly, in accordance with an embodiment.

Referring to FIG. 16, a side view of a distal portion of a biostimulator having a removed header assembly is shown in accordance with an embodiment. The inner pinch point 404 can be between the proximal turn 1502 and the helical coil section 706 that extends from the proximal turn 1502 to the second distal tip 220. In an embodiment, the proximal turn 1502 is an annular element extending along a transverse plane. For example, the proximal turn 1502 can be a tubular segment or C-shaped segment that is flat and circular about the longitudinal axis 208 (as opposed to helical). The helical portion of the inner fixation element 218 can extend distally from the flat or C-shaped proximal turn 1502.

As described above, a longitudinal location of the inner pinch point 404 can be tightly controlled, e.g., to be proximal to the outer pinch point 328. The inclusion of the proximal turn 1502 to permit the butt weld 402 to the cup 516 can add an overall vertical height to the inner fixation element 218 relative to the embodiment shown in FIG. 4-5. To compensate for the increased height and maintain the relative longitudinal position of the inner pinch point 404 relative to the outer pinch point 328, a height of the cup 516 may be reduced. More particularly, a height of the electrode wall 534 of the cup 516 may be reduced by the same distance as the height of the proximal turn 1502. Accordingly, the second distal tip 220 of the embodiment shown in FIG. 16 can have a same vertical location relative to the first distal tip 216, as the embodiment shown in FIG. 5.

A portion of the inner fixation element 218 may fit within the cavity of the cup 516. More particularly, the inner fixation element 218 may include a first portion that fits within the cup 516 and a second portion having an outer dimension that is too large to fit within the cup 516. Accordingly, the inner fixation element 218 can have a variable inner or outer diameter, e.g., an outer diameter that varies over a length of the inner fixation element 218. The outer diameter of a proximal portion of the inner fixation element 218 can be less than an inner diameter of the cup 516 cavity, and an outer diameter of the distal portion of the inner fixation element 218 can be greater than the inner diameter of the cup cavity.

Figure 17:
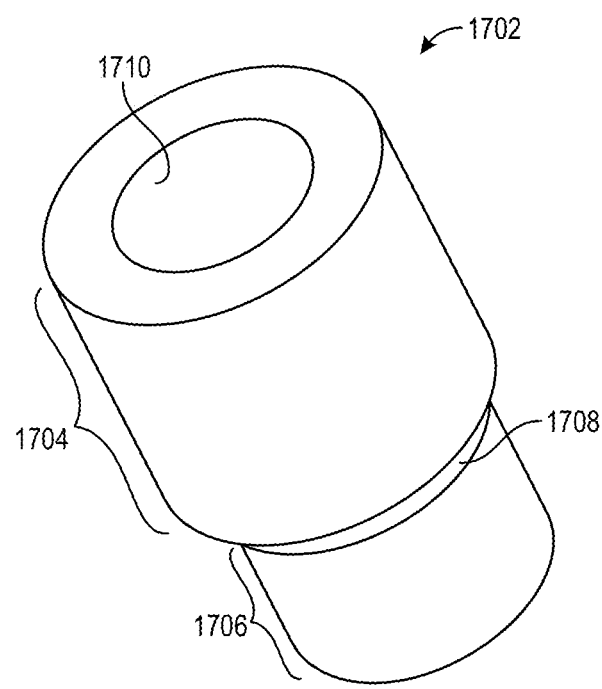
FIG. 17 is a perspective view of a tube used to form a fixation element, in accordance with an embodiment.

Referring to FIG. 17, a perspective view of a tube used to form a fixation element is shown in accordance with an embodiment. A variable diameter inner fixation element 218 can be formed from bell-mouth tubing 1702. The bell-mouth tubing 1702 can have a distal segment 1704 and a proximal segment 1706. The distal segment 1704 can have an outer dimension, e.g., an outer diameter, that is greater than an outer dimension of the proximal segment 1706. Accordingly, the proximal segment 1706 can transition to the distal segment 1704 at a transition zone 1708. The transition zone 1708 can be a step, a taper, etc. The bell-mouth tubing 1702 can have a constant wall thickness over a length, and thus, an inner lumen 1710 of the bell-mouth tubing 1702 can vary along with the outer diameters of the distal segment 1704 and the proximal segment 1706. More particularly, the inner diameter of the distal segment 1704 can be greater than the inner diameter of the proximal segment 1706. Alternatively, the tubing may have a variable outer diameter and a constant inner diameter over the length. For example, the tubing can be a cylindrical tube that is centerless ground to form the proximal segment 1706 having the smaller outer diameter, however, the inner diameter may be constant through the entire length of the inner fixation element 218.

Figure 18:
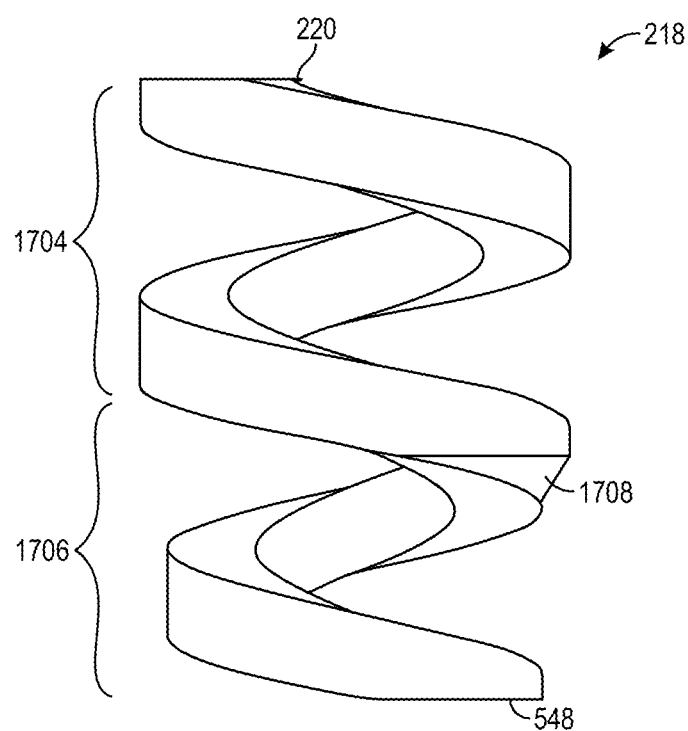
FIG. 18 is a side view of a fixation element having a variable diameter, in accordance with an embodiment.

Referring to FIG. 18, a side view of a fixation element having a variable diameter is shown in accordance with an embodiment. The variable dimension tubing, e.g., the bell-mouth tubing 1702, can be cut to form the inner fixation element 218. For example, the tubing can be laser cut to form a helical slot that reveals the helical form of the fixation element. As described above, the laser cut fixation element can have a quadrilateral, e.g., rectangular, cross-sectional area. The cross-sectional area can extend along the inner helix 302 from the flat proximal end 548 to the second distal tip 220.

The inner fixation element 218 formed from the variable dimension tubing can have some of the same characteristics as the raw tubing. For example, the inner fixation element 218 can include the proximal segment 1706 and distal segment 1704. The proximal segment 1706 can have a smaller outer diameter than the distal segment 1704, and thus, the proximal segment 1706 may fit within the cavity of the cup 516 while the distal segment 1704 may be unable to fit into the cup 516 and extends distally from the distal cup end 406. The proximal segment 1706 can transition to the distal segment 1704 at the transition zone 1708.

Figure 19:
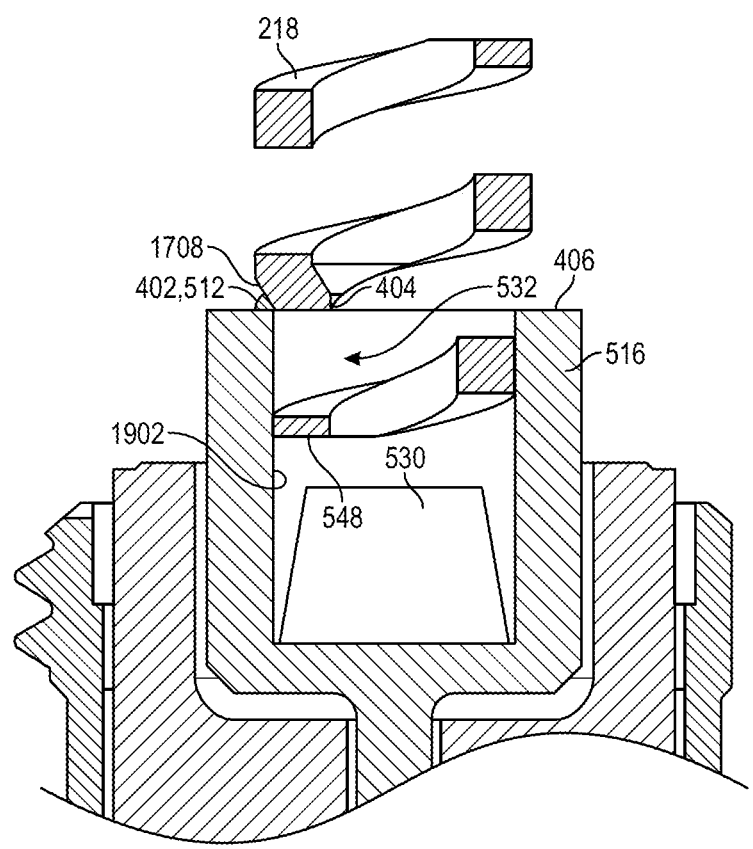
FIG. 19 is a cross-sectional view of a distal portion of a biostimulator having a removed header assembly, in accordance with an embodiment.

Referring to FIG. 19, a cross-sectional view of a distal portion of a biostimulator having a removed header assembly is shown in accordance with an embodiment. The inner fixation element 218 having the variable outer dimension can be inserted into the electrode cavity 532 of the cup 516. When the proximal segment 1706 of the inner fixation element 218 is shorter in length than a height of the cavity within the cup 516, the transition zone 1708 can therefore abut the distal cup end 406. The transition zone 1708 therefore acts as a stop and a longitudinal position control for the inner fixation element 218. In other words, the inner fixation element 218 can be fit into the cup 516 having a straight inner wall 1902 without having the proximal end 548 bottom out on filler 530. As described above, the inner dimension 552 of the inner fixation element 218 can be less than an outer dimension of the filler 530, and thus, the inner fixation element 218 can retain the filler 530 within the cup 516.

The inner fixation element 218 can be joined to the cup 516 by the weld 402. The weld 402 can be a spot weld 512 to fix the fixation element 106 to the cup 516 as described above. The spot weld 512 can fill the angled recess formed between the transition zone 1708 and the distal cup end 406. Accordingly, a strong joint between the inner fixation element 218 and the cup 516 can be formed to resist mechanical fatigue and to allow the components to act as a unitary body. When the inner fixation element 218 is loaded into and joined to the cup 516, the inner pinch point 404 can be between a turn of the inner fixation element 218 and the distal cup end 406. Accordingly, as the inner fixation element 218 is screwed into the target tissue, the tissue can be stopped and retained at the inner pinch point 404.

A biostimulator, such as a leadless cardiac pacemaker, including coaxial fixation elements to engage or electrically stimulate tissue, has been described. In an embodiment, the biostimulator includes a housing having a longitudinal axis and containing an electronics compartment. The biostimulator includes an outer fixation element coupled to the housing. The outer fixation element includes an outer helix extending about the longitudinal axis to a first distal tip. The biostimulator includes an inner fixation element coupled to the housing. The inner fixation element includes an inner helix radially inward of the outer helix and extending about the longitudinal axis to a second distal tip. The first distal tip is distal to the second distal tip.

In an embodiment, a first stiffness of the outer fixation element in a direction of the longitudinal axis is less than a second stiffness of the inner fixation element in the direction.

In an embodiment, the outer fixation element has a lower spring constant than the inner fixation element.

In an embodiment, a first pitch of the outer helix is equal to a second pitch of the inner helix.

In an embodiment, the biostimulator includes a helix mount and a cup. The outer fixation element is mounted on the helix mount. The inner fixation element is mounted on the cup.

In an embodiment, the helix mount includes a central opening extending along the longitudinal axis. The inner fixation element extends through the central opening from the cup to the second distal tip. The central opening widens from a proximal edge to a distal edge of the helix mount such that a distal dimension of the central opening is greater than a proximal dimension of the central opening.

In an embodiment, the helix mount includes a chamfer surface extending from the proximal edge to the distal edge around the central opening.

In an embodiment, the cup includes an electrode wall extending distally from an electrode base around an electrode cavity located on the longitudinal axis. The electrode cavity includes a proximal cavity coaxial with a distal counterbore having a ledge.

In an embodiment, the biostimulator includes a filler in the proximal cavity. The inner fixation element has a proximal end mounted on the ledge of the distal counterbore.

In an embodiment, the filler has a filler dimension that is greater than an inner dimension of the inner fixation element.

In an embodiment, the filler includes a therapeutic agent in a silicone matrix.

In an embodiment, the housing includes a flange having interrupted external threads.

In an embodiment, the interrupted external threads are tapped into an inner surface of the helix mount to connect the helix mount to the flange.

In an embodiment, the helix mount includes a helix mount flange extending around the longitudinal axis to a flange notch. The outer fixation element is mounted on the helix mount flange such that an outer pinch point between the outer fixation element and the helix mount flange is at the flange notch.

In an embodiment, the helix mount flange includes a secondary fixation channel extending from a first opening on a radially outward surface of the helix mount flange to a second opening on the radially outward surface.

In an embodiment, at least a portion of one or more of the outer fixation element or the inner fixation element are formed from a biodegradable material.

In an embodiment, the biodegradable material is a metal.

In an embodiment, the inner fixation element has a helical coil section and a flat coil section.

In an embodiment, the first distal tip of the outer fixation element is on a first side of a first plane containing the longitudinal axis and the second distal tip of the inner fixation element is on a second side of the first plane opposite of the first distal tip.

In an embodiment, a second plane containing the longitudinal axis, the first distal tip, and the second distal tip is orthogonal to the first plane.

In an embodiment, a leadless biostimulator system includes a transport system including a catheter having a distal end, and a leadless biostimulator coupled to the distal end. The leadless biostimulator includes a housing having a longitudinal axis and containing an electronics compartment. The leadless biostimulator includes an outer fixation element coupled to the housing. The outer fixation element includes an outer helix extending about the longitudinal axis to a first distal tip. The leadless biostimulator includes an inner fixation element coupled to the housing. The inner fixation element includes an inner helix radially inward of the outer helix and extending about the longitudinal axis to a second distal tip. The first distal tip is distal to the second distal tip.

In an embodiment, a biostimulator includes a housing having a longitudinal axis and containing an electronics compartment. The biostimulator includes an outer fixation element coupled to the housing. The outer fixation element includes an outer helix extending about the longitudinal axis to a first distal tip. The biostimulator includes an inner fixation element coupled to the housing. The inner fixation element includes an inner helix radially inward of the outer helix and extending about the longitudinal axis to a second distal tip. The inner fixation element is an electrode of the biostimulator.

In an embodiment, a first stiffness of the outer fixation element in a direction of the longitudinal axis is less than a second stiffness of the inner fixation element in the direction.

In an embodiment, the outer fixation element has a lower spring constant than the inner fixation element.

In an embodiment, a first pitch of the outer helix is equal to a second pitch of the inner helix.

In an embodiment, the biostimulator includes a helix mount and a cup. The outer fixation element is mounted on the helix mount. The inner fixation element is mounted on the cup.

In an embodiment, the helix mount includes a central opening extending along the longitudinal axis. The inner fixation element extends through the central opening from the cup to the second distal tip. The central opening widens from a proximal edge to a distal edge of the helix mount such that a distal dimension of the central opening is greater than a proximal dimension of the central opening.

In an embodiment, the helix mount includes a chamfer surface extending from the proximal edge to the distal edge around the central opening.

In an embodiment, the cup includes an electrode wall extending distally from an electrode base around an electrode cavity located on the longitudinal axis. The electrode cavity includes a proximal cavity coaxial with a distal counterbore having a ledge.

In an embodiment, the biostimulator includes a filler in the proximal cavity. The inner fixation element has a proximal end mounted on the ledge of the distal counterbore.

In an embodiment, the filler has a filler dimension that is greater than an inner dimension of the inner fixation element.

In an embodiment, the filler includes a therapeutic agent in a silicone matrix.

In an embodiment, the housing includes a flange having interrupted external threads.

In an embodiment, the interrupted external threads are tapped into an inner surface of the helix mount to connect the helix mount to the flange.

In an embodiment, the helix mount includes a helix mount flange extending around the longitudinal axis to a flange notch. The outer fixation element is mounted on the helix mount flange such that an outer pinch point between the outer fixation element and the helix mount flange is at the flange notch.

In an embodiment, the helix mount flange includes a secondary fixation channel extending from a first opening on a radially outward surface of the helix mount flange to a second opening on the radially outward surface.

In an embodiment, at least a portion of one or more of the outer fixation element or the inner fixation element are formed from a biodegradable material.

In an embodiment, the biodegradable material is a metal.

In an embodiment, the inner fixation element has a helical coil section and a flat coil section.

In an embodiment, the first distal tip of the outer fixation element is on a first side of a first plane containing the longitudinal axis and the second distal tip of the inner fixation element is on a second side of the first plane opposite of the first distal tip.

In an embodiment, a second plane containing the longitudinal axis, the first distal tip, and the second distal tip is orthogonal to the first plane.

In an embodiment, a leadless biostimulator system includes a transport system including a catheter having a distal end, and a leadless biostimulator coupled to the distal end. The leadless biostimulator includes a housing having a longitudinal axis and containing an electronics compartment. The leadless biostimulator includes an outer fixation element coupled to the housing. The outer fixation element includes an outer helix extending about the longitudinal axis to a first distal tip. The leadless biostimulator includes an inner fixation element coupled to the housing. The inner fixation element includes an inner helix radially inward of the outer helix and extending about the longitudinal axis to a second distal tip. The inner fixation element is an electrode of the biostimulator.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A leadless biostimulator, comprising:
a housing having a longitudinal axis and an electronics compartment containing pacing circuitry; and
a header assembly mounted on the housing, wherein the header assembly includes
an outer fixation element having an outer helix extending about the longitudinal axis in a helical direction to a first distal tip, and
an inner fixation element having an inner helix radially inward of the outer helix and extending about the longitudinal axis in the helical direction to a second distal tip, and wherein the first distal tip is distal to the second distal tip.

2. The biostimulator of claim 1, wherein a first stiffness of the outer fixation element in a longitudinal direction of the longitudinal axis is less than a second stiffness of the inner fixation element in the longitudinal direction.

3. The biostimulator of claim 2, wherein the outer fixation element has a lower spring constant than the inner fixation element.

4. The biostimulator of claim 2, wherein a first pitch of the outer helix is equal to a second pitch of the inner helix.

5. The biostimulator of claim 1 further comprising a helix mount and a cup, wherein the outer fixation element is mounted on the helix mount, and wherein the inner fixation element is mounted on the cup.

6. The biostimulator of claim 5, wherein the helix mount includes a central opening extending along the longitudinal axis, wherein the inner fixation element extends through the central opening from the cup to the second distal tip, and wherein the central opening widens from a proximal edge to a distal edge of the helix mount such that a distal dimension of the central opening is greater than a proximal dimension of the central opening.

7. The biostimulator of claim 6, wherein the helix mount includes a chamfer surface extending from the proximal edge to the distal edge around the central opening.

8. The biostimulator of claim 5, wherein the cup includes an electrode wall extending distally from an electrode base around an electrode cavity located on the longitudinal axis, and wherein the electrode cavity includes a proximal cavity coaxial with a distal counterbore having a ledge.

9. The biostimulator of claim 8 further comprising a filler in the proximal cavity, and wherein the inner fixation element has a proximal end mounted on the ledge of the distal counterbore.

10. The biostimulator of claim 9, wherein the filler has a filler dimension that is greater than an inner dimension of the inner fixation element.

11. The biostimulator of claim 9, wherein the filler includes a therapeutic agent in a silicone matrix.

12. The biostimulator of claim 5, wherein the housing includes a flange having interrupted external threads.

13. The biostimulator of claim 12, wherein the interrupted external threads are tapped into an inner surface of the helix mount to connect the helix mount to the flange.

14. The biostimulator of claim 5, wherein the helix mount includes a helix mount flange extending around the longitudinal axis to a flange notch, and wherein the outer fixation element is mounted on the helix mount flange such that an outer pinch point between the outer fixation element and the helix mount flange is at the flange notch.

15. The biostimulator of claim 14, wherein the helix mount flange includes a secondary fixation channel extending from a first opening on a radially outward surface of the helix mount flange to a second opening on the radially outward surface.

16. The biostimulator of claim 1, wherein at least a portion of one or more of the outer fixation element or the inner fixation element are formed from a biodegradable material.

17. The biostimulator of claim 16, wherein the biodegradable material is a metal.

18. The biostimulator of claim 1, wherein the inner fixation element has a helical coil section and a flat coil section.

19. The biostimulator of claim 1, wherein the first distal tip of the outer fixation element is on a first side of a first plane containing the longitudinal axis and the second distal tip of the inner fixation element is on a second side of the first plane opposite of the first distal tip.

20. The biostimulator of claim 19, wherein a second plane containing the longitudinal axis, the first distal tip, and the second distal tip is orthogonal to the first plane.

21. A leadless biostimulator system, comprising:
a transport system including a catheter having a distal end; and
a leadless biostimulator coupled to the distal end and including
a housing having a longitudinal axis and an electronics compartment containing pacing circuitry, and
a header assembly mounted on the housing, wherein the header assembly includes
an outer fixation element having an outer helix extending about the longitudinal axis in a helical direction to a first distal tip, and
an inner fixation element having an inner helix radially inward of the outer helix and extending about the longitudinal axis in the helical direction to a second distal tip, and wherein the first distal tip is distal to the second distal tip.

* * * * *